US012653858B2

(12) United States Patent
Hsu et al.

(10) Patent No.: US 12,653,858 B2
(45) Date of Patent: Jun. 16, 2026

(54) HERBAL COMPOSITION, PREPARATION METHOD THEREOF AND METHOD FOR PREVENTING OR TREATING RESPIRATORY DISORDER BY ADMINISTERING THE SAME

(71) Applicants:National Yang Ming Chiao Tung University, Taipei (TW); Taipei City Hospital, Taipei (TW)

(72) Inventors: Chung-Hua Hsu, Taipei City (TW); Shu-Ling Fu, Taipei (TW); Tung-Yi Lin, Taipei (TW); Yueh-Hsin Ping, Taipei (TW)

(73) Assignees: National Yang Ming Chiao Tung University, Taipei City (TW); Taipei City Hospital, Taipei (TW)

( * ) Notice: Subject to any disclaimer, the term of this patent is extended or adjusted under 35 U.S.C. 154(b) by 648 days.

(21) Appl. No.: 18/056,988

(22) Filed: Nov. 18, 2022

(65) Prior Publication Data

US 2023/0149494 A1 May 18, 2023

Related U.S. Application Data

(60) Provisional application No. 63/280,635, filed on Nov. 18, 2021.

(51) Int. Cl.
| | |
|---|---|
| *A61K 36/634* | (2006.01) |
| *A61K 36/233* | (2006.01) |
| *A61K 36/284* | (2006.01) |
| *A61K 36/532* | (2006.01) |
| *A61K 36/539* | (2006.01) |
| *A61K 36/575* | (2006.01) |
| *A61K 36/638* | (2006.01) |
| *A61P 31/14* | (2006.01) |

(52) U.S. Cl.
CPC .......... *A61K 36/634* (2013.01); *A61K 36/233* (2013.01); *A61K 36/284* (2013.01); *A61K 36/532* (2013.01); *A61K 36/539* (2013.01); *A61K 36/575* (2013.01); *A61K 36/638* (2013.01); *A61P 31/14* (2018.01); *A61K 2236/331* (2013.01); *A61K 2236/333* (2013.01)

(58) Field of Classification Search
None
See application file for complete search history.

(56) References Cited

FOREIGN PATENT DOCUMENTS

CN        110575521 A    * 12/2019    ......... A61K 36/9068

OTHER PUBLICATIONS

Shahrajabian, M.H., et al., The Function of some Important TCM and Iranian Medicinal Plants in Treatment of Viral Hepatitis, Pharmacogn. Commn. 2021;11(2):100-108, Apr.-Jun. 2021 (Year: 2021).*
Machine translation of CN-110575521-A.*

* cited by examiner

*Primary Examiner* — H. Sarah Park
(74) *Attorney, Agent, or Firm* — HSML P.C.

(57) ABSTRACT

Provided is an herbal composition including an extract from a combination of herbs including at least five of *Forsythia suspensa, Scutellaria baicalensis, Bupleurum chinese, Magnolia officinalis, Agastache rugosa, Astragalus membranaceus, Atractylodes macrocephala*, and seeds of *Ligustrum lucidum*. Also provided is a method for preparing the herbal composition and a method for preventing or treating a viral infection by administering an effective amount of the herbal composition to a subject in need thereof.

12 Claims, 38 Drawing Sheets
(4 of 38 Drawing Sheet(s) Filed in Color)
Specification includes a Sequence Listing.

RAW264.7-24h

RAW264.7-24h

RAW264.7-24h

RAW264.7-24h

RAW264.7-24h

RAW264.7-24h

RAW264.7-24h

RAW264.7-24h

RAW264.7-24h

RAW264.7-24h

HERBAL COMPOSITION, PREPARATION METHOD THEREOF AND METHOD FOR PREVENTING OR TREATING RESPIRATORY DISORDER BY ADMINISTERING THE SAME

TECHNICAL FIELD

The present disclosure relates to herbal compositions, and in particular relates to herbal compositions for preventing or treating respiratory disorder caused by viral infections.

SEQUENCE LISTING

The present application is being filed along with a Sequence Listing in electronic format. The Sequence Listing is provided as a file entitled 210972US-Sequence listing. XML, created on Apr. 6, 2023, which is 4,588 bytes (about 4.489 KB) in size. The information in the electronic format of Sequence Listing is incorporated herein by reference in its entirety.

BACKGROUND

Coronaviruses (CoVs) are a large family of viruses that can cause illness of the respiratory system and result in symptoms ranging from those similar to common cold to severe and complex respiratory system failure. Many human coronavirus strains have been identified, such as CoV-229E, CoV-OC43, CoV-NL63, and CoV-HKU1, which usually result in mild, self-limiting upper respiratory tract infections, such as asymptomatic infection or a mild, flu-like illness, e.g., runny nose, sneezing, headache, cough, sore throat, and fever. However, the past decades saw several pandemics such as severe acute respiratory syndrome (SARS), Middle East respiratory syndrome (MERS), and the most recent coronavirus disease 2019 (COVID-19) that are caused by strains of CoVs leading to severe acute respiratory syndrome such as severe pneumonia and even death. Until mid-May 2021, more than 162 million COVID-19 cases were recorded worldwide with a death toll of more than 3.3 million cases. The disease has serious impact on societies and lives of people in the world and threats the economics worldwide.

Until now, there is still no specific antiviral treatment available or proven to be effective to treat or prevent coronavirus infection in a subject. While several vaccines have been approved and used, there remain certain percentage of severe side effects such as blood clots, myocarditis and other serious ailments.

Therefore, there exists an unmet need to provide an effective and safe therapeutics to prevent or treat coronavirus infections.

SUMMARY

In view of the foregoing, the present disclosure provides an herbal composition that is capable of inducing degradation of ACE2 on the host cell surface, and suppressing the expression of proteins that are necessary for entry and replication of coronavirus in a host thereof, thereby preventing and protecting a subject from a viral infection.

In at least one embodiment of the present disclosure, the herbal composition for preventing or treating a viral infection comprises a decoction of a combination of herbs and a pharmaceutically acceptable carrier thereof, wherein the combination of herbs comprises at least five selected from the group consisting of Lianqiao (*Forsythia suspensa*), Huangqin (*Scutellaria baicalensis*), Chaihu (*Bupleurum Chinese*), Houpo (*Magnolia officinalis*), Huoxiang (*Agastache rugosa*), Huangqi (*Astragalus membranaceus*), Baizhu (*Atractylodes macrocephala*), and Nvzhenzi (seeds of *Ligustrum lucidum*). In at least one embodiment, the herbal decoction is a water extract or an ethanol extract. In at least one embodiment, the herbal composition comprises a decoction obtained from the combination of herbs comprising, based on a total weight thereof, 25% to 35% by weight of *Forsythia suspensa,* 18% to 26% by weight of *Scutellaria baicalensis,* 15% to 25% by weight of *Bupleurum Chinese,* 15% to 25% by weight of *Magnolia officinalis,* 7% to 15% by weight of *Agastache rugosa,* 1% to 5% by weight of *Astragalus membranaceus,* 1% to 5% by weight of seeds of *Ligustrum lucidum* and 1% to 5% by weight of *Atractylodes macrocephala.* In at least one embodiment, the herbal composition comprises a decoction extracted from a combination of herbs comprising 8 mg to 10 mg of *Forsythia suspensa,* 6 mg to 8 mg of *Scutellaria baicalensis,* 4 mg to 6 mg of *Bupleurum Chinese,* 4 mg to 6 mg of *Magnolia officinalis* and 1 mg to 3 mg of *Agastache* rugosa.

In at least one embodiment of the present disclosure, a method for preparing the herbal composition is provided, comprising providing a combination of herbs including at least five of *Forsythia suspensa, Scutellaria baicalensis, Bupleurum Chinese, Magnolia officinalis, Agastache rugosa, Astragalus membranaceus, Atractylodes macrocephala,* and seeds of *Ligustrum lucidum;* extracting the herbs with an extracting solution including at least one of water and ethanol by boiling; and removing solid from the extract to obtain a decoction. In at least one embodiment, the extracting comprises boiling the herbal combination in the extracting solution for at least an hour, including 2 hours, 3 hours, and 4 hours, but not limited thereto. In at least one embodiment, the extracting comprises boiling the herbal combination in the extracting solution at a temperature of at least 70° C., including a temperature of 80° C., 90° C., 100° C., 110° C. and 120° C. In at least one embodiment, the extracting comprises boiling the herbal combination in the extracting solution at an atmospheric pressure of at least 1 atm, including 1.1 atm, 1.2 atm and 1.3 atm, but not limited thereto. In at least one embodiment, the method comprises extracting from the herbal combination having a weight ratio to the extracting solution from 0.5:1 to 5:1.

In at least one embodiment of the present disclosure, extracting the herbal decoction comprises boiling the herbal raw material (i.e., a combination of herbs) in the extracting solution for at least an hour, such as 1 hour to 6 hours, and/or immersing the herbal raw material in the extracting solution with a temperature around a boiling point for at least an hour, such as 1 hour to 6 hours. In some embodiments, the weight ratio of the herbal raw material to the extracting solution is from 0.5:1 to 5:1, such as 1:1, 2:1, 3:1, 4:1 and 5:1.

In at least one embodiment of the present disclosure, the method for preparing the herbal composition further comprises concentrating the liquid portion to obtain a concentrated extract.

In at least one embodiment of the present disclosure, a method for preventing or treating a viral infection in a subject in need thereof is provided. The method comprises administering to the subject an effective amount of at least one of the above-mentioned herbal compositions.

In at least one embodiment of the present disclosure, the viral infection is caused by a coronavirus. In some embodiments, the coronavirus is SARS-CoV, MERS-CoV, SARS- CoV-2, mouse hepatitis virus (MHV), or porcine epidemic diarrhea virus (PEDV). In some embodiments, the coronavirus is a variant of SARS-CoV-2, such as a D614G mutant strain, a B.1.1.7 (Alpha) mutant strain, a B.1.351 (Beta) mutant strain, and a P1 mutant strain, but not limited thereto.

In at least one embodiment of the present disclosure, the extract from the herbal raw material in the herbal composition is administered to the subject in an effective amount of from about 25 g/week to about 1,000 g/week, such as from about 50 g/week to about 800 g/week, and from about 100 g/week to about 500 g/week.

In the present disclosure, the herbal composition provided in the present disclosure as an antivirus agent may inhibit virus replication and reduce the number of viruses in a host cell. In addition, the herbal composition provided in the present disclosure is safe and may solve the prior-art problems of side effects. Hence, the present disclosure provides an effective strategy against viral infections, which is useful in controlling the outbreak of coronaviruses.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure can be more fully understood by reading the following descriptions of the embodiments, with reference made to the accompanying drawings.

FIG. 1A examines the cytotoxicity of the herbal compositions of the JGF. BHK-21 and Calu-3 cells were treated with indicated amounts of the herbal compositions, and cell viability was examined by lactate dehydrogenase (LDH) assay. The control group represented the non-treatment group, serving as a negative control. The treatment with Triton-100 was used as a positive control. The data were presented as the mean±SD; error bars indicated SD. n.s. indicated non-significant, compared to the control group. FIG. 1B shows the expression of ACE2 in Calu-3 cells treated with 40 μg/mL of JGF analyzed by Western blotting assay (upper panel). The level of ACE2 expression was quantified after normalization with α-tubulin. The quantification analysis from three independent experiments was shown in bottom panel. * represents P<0.05. FIG. 1C shows the cell-cell fusion of SARS-CoV-2 S protein-expressing BHK-21 cells and ACE2-expressing Calu-3 cells visualized in the presence of indicated amounts of JGF. FIG. 1D quantifies the formation of syncytium under various concentrations of JGF. Compared with the control, syncytium formation was significantly inhibited for 20 to 80 μg/mL JGF treatments. * represents P<0.05.

FIG. 3A shows the WI-38 and MRC-5 cells treated with three dosages of JGF (0 to 20 μg/mL) for 3 and 24 h. Western blotting was subsequently performed with whole cell lysates to detect expression of ACE2. Actin was used as the internal control. FIG. 3B shows the quantification of the intensities of the bands of ACE2 in FIG. 3A which are representative of three separate determinations using ImageJ (National Institute of Mental Health, Bethesda, MD, USA). The data were presented as the mean±SD; error bars indicated SD. Significant differences were shown (* P<0.05 compared to the control group). FIG. 3C shows the time course for ACE2 degradation after the addition of cycloheximide (CHX; 100 μg/mL) in the presence or absence of JGF (10 μg/mL) for 0 to 180 mins in WI-38 cells, as analyzed by Western blotting. Shown in the curve to the right are levels of ACE2 in the three-independent experiments quantified by ImageJ, and the results were presented as the mean±SD; error bars indicate SDs. Significant differences were shown (* P<0.05 compared to the control DMSO group). FIG. 3D shows the Western blotting result of WI-38 cells pretreated with DMSO (vehicle control) or BafA1 (10 μM) for 30 min, followed by incubation with JGF (10 μg/mL) for 2 h, and FIG. 3E shows the quantification bar graph of the Western blotting in FIG. 3D. Western blotting was subsequently performed with whole cell lysates to detect expression of ACE2. Actin was used as the internal control.

FIG. 4A shows the WI-38 and MRC-5 cells treated with JGF (0 to 20 μg/mL) for 3 and 24 h. Western blotting was subsequently performed with whole cell lysates to detect the expression of TMPRSS2. Actin was used as the internal control. FIG. 4B shows the quantification of the intensities of the bands of TMPRSS2 shown in FIG. 4A, which was representative of three separated determinations by ImageJ. FIG. 4C shows the WI-38 and MRC-5 cells treated with JGF (0, 10 and 20 μg/mL) for 24 h. The mRNA levels of TMPRSS2 were determined by qRT-PCR. The data were presented as the mean±SD; error bars indicated SD. Significant differences were shown (* P<0.05 compared to the control group).

FIG. 5A shows the experiment scheme for mouse receiving JGF via oral gavage. FIG. 5B shows the ACE2 and TMPRSS2 levels in lung tissues of mice receiving JGF via oral gavage. FIG. 5C shows the experiment scheme for mouse receiving JGF via the steam spray method. FIG. 5D shows the ACE2 and TMPRSS2 levels in lung tissue of mice receiving JGF via steam spray. FIG. 5E shows the body weight changes (%) for mice receiving JGF via oral gavage every other day. FIGS. 5F and 5G show the measures of hepatic function (AST and ALT) and renal function (BUN and Creatinine) of mice sera analyzed on Day 1 and Day 17, respectively. FIGS. 5H and 5I show the effect of the herbal compositions of the JGF on ACE2 and TMPRSS2 levels in other tissues including kidney, cortex and colon, after the experiments shown in FIGS. 5A and 5C, respectively, and no significant difference of expression levels was observed.

FIG. 6A shows the cell viability of Vero E6 cells treated with various concentrations of JGF (0 to 800 μg/mL) for 72 h. Each group of JGF-treated samples was normalized against an untreated control. Cell viability was determined using the MTT assay. FIG. 6B shows the experiment scheme where Vero E6 cells were pre-treated with JGF (0 to 200 μg/mL) for 1 h and then infected with

5

Figure 6A:
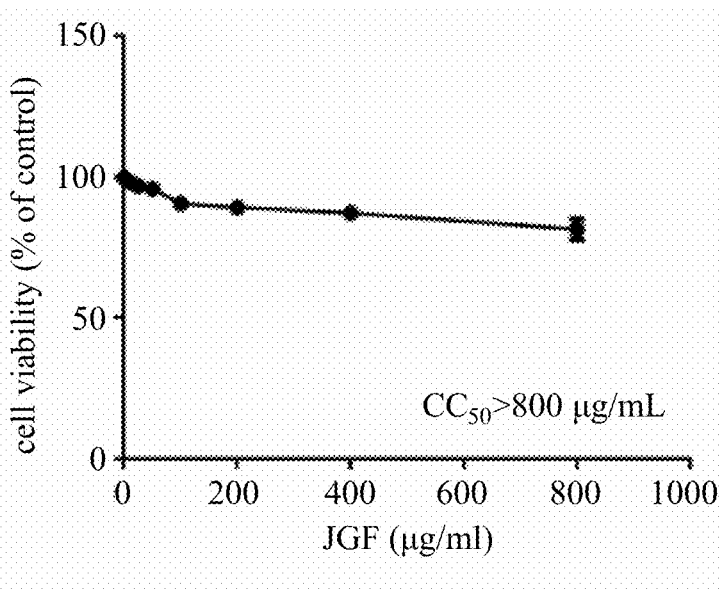
FIGS. 6A to 6C illustrate the inhibitory effect of the herbal compositions of the JGF on plaque formation of SARS-CoV-2 in Vero E6 cells.
Figure 6B:
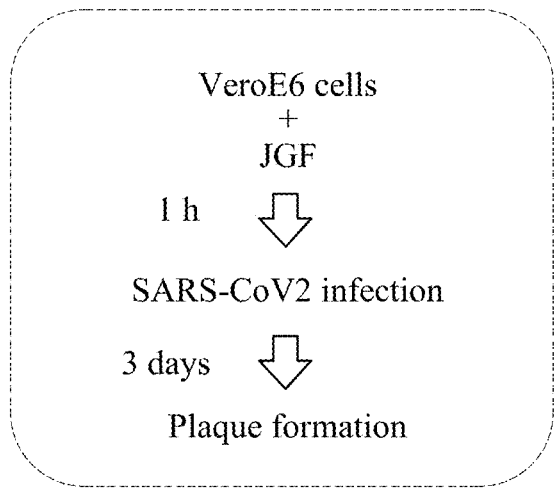
Figure 6C:
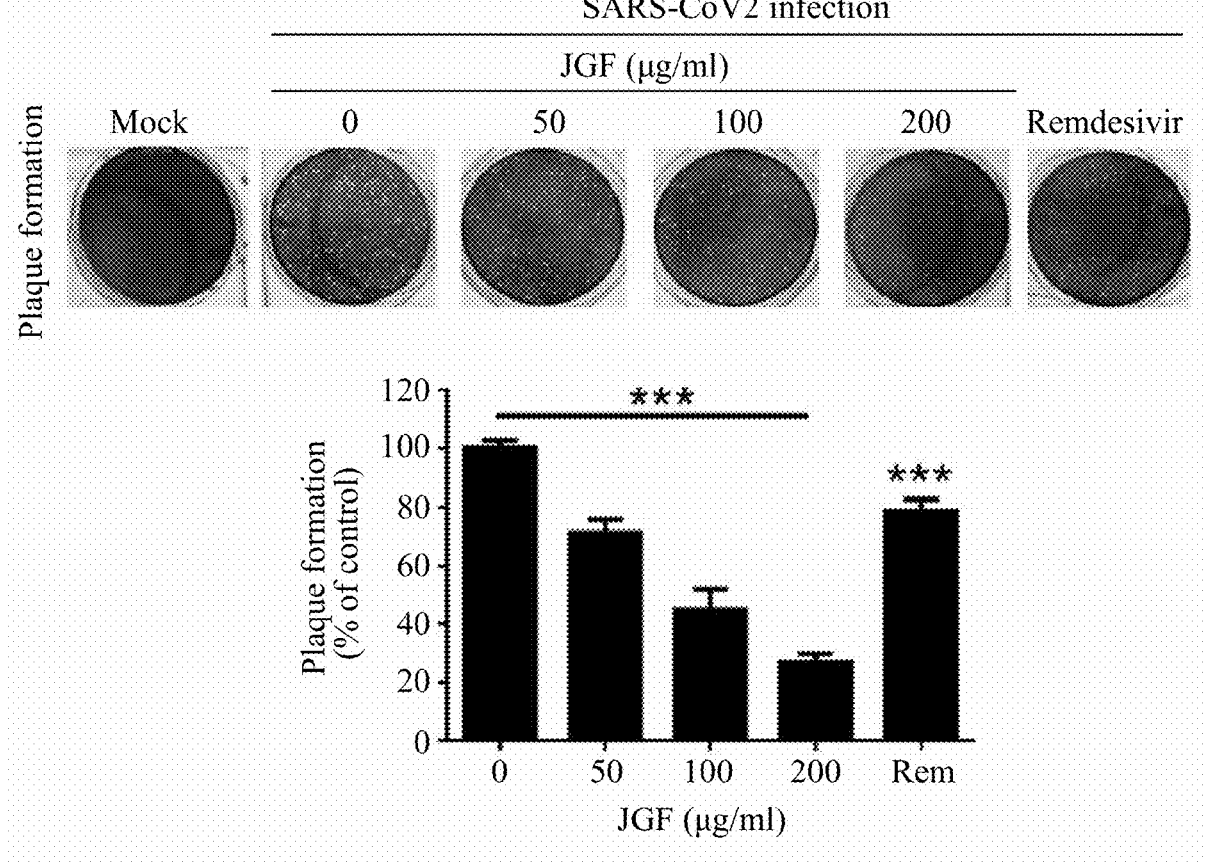

SARS-CoV-2 for 3 days. FIG. 6C shows the result of the experiment where plaque was stained with crystal violet. In the quantification bar graph, data were representative of three separate experiments and were presented as the mean±SD; error bars indicated SDs.

Figure 7:
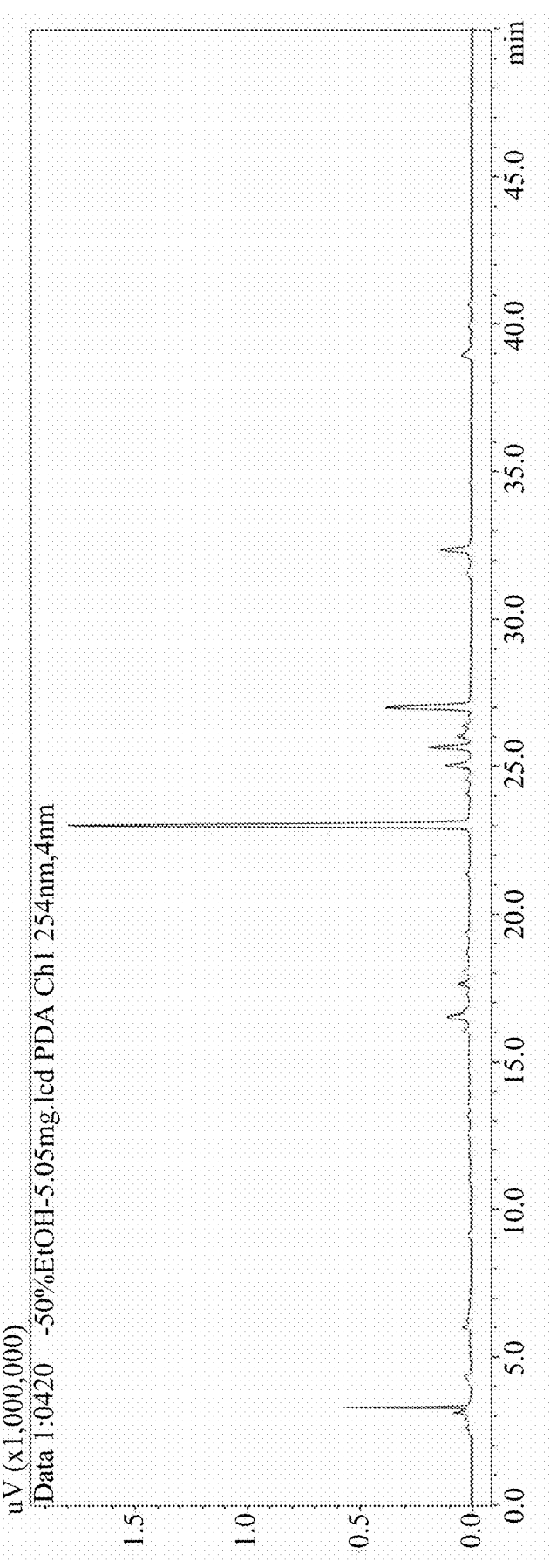

FIG. 7 shows the HPLC fingerprint of the herbal composition of the JGF under UV 254 nm detection. Peak 1: baicalin, retention time (rt)=23.0 min; peak 2: wagonin-7-O-glucuronide, rt=25.6 min; peak 3: wagonin-7-O-glucose, rt=27.0 min; peak 4: baicalein, rt=32.4 min.

Figure 8:
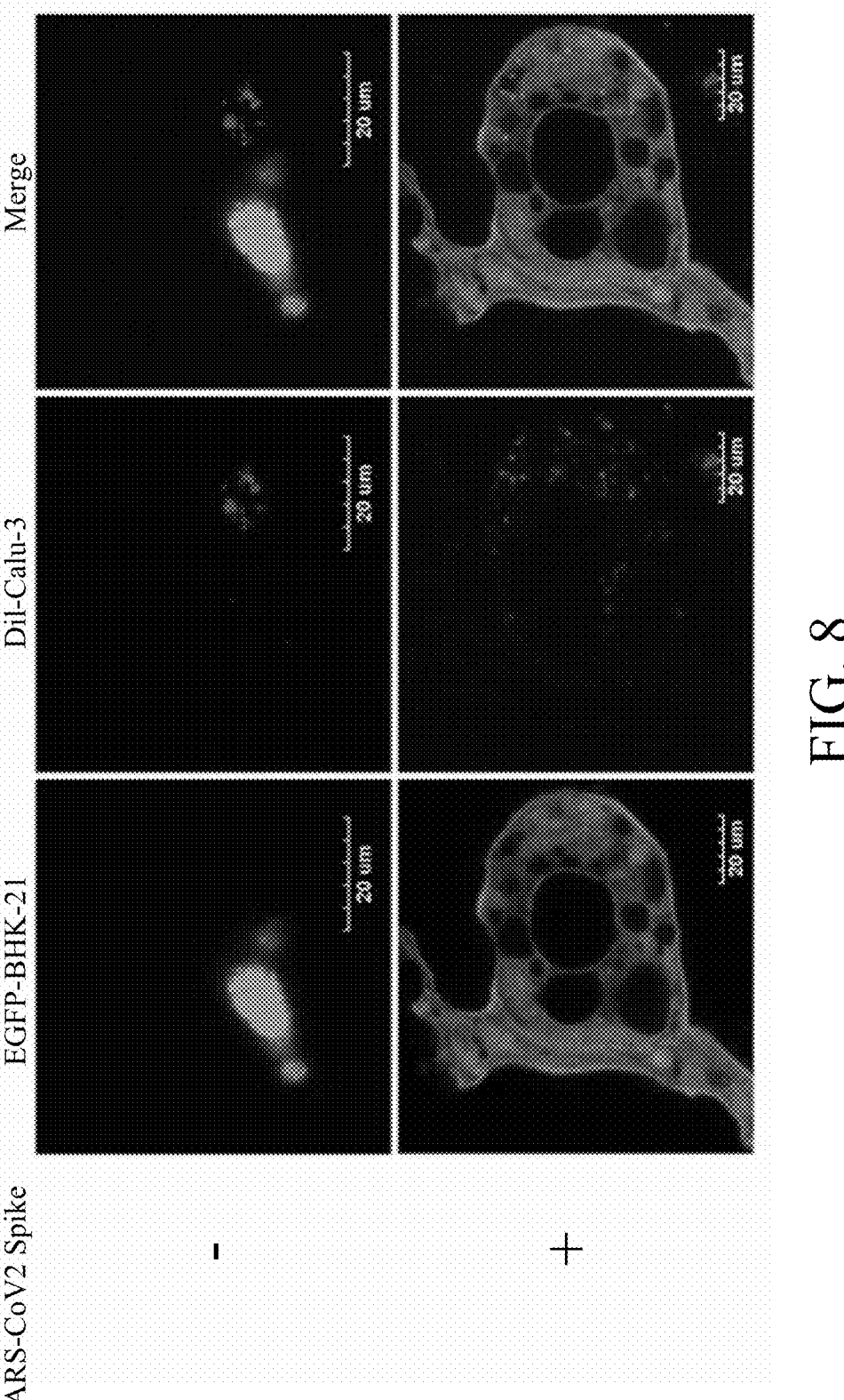

FIG. 8 shows the confocal images depicting eGFP expressing BHK-21 cells as green and DiI-labeled Calu-3 cells as red. In the absence of SARS-CoV-2 S protein, eGFP-expressing BHK-21 cells could attach but not fuse with Calu-3 cells. When eGFP and SARS-CoV-2 spike proteins are co-expressed in BHK-21 cells, BHK-21 could fuse with DiI-labeled Calu-3 cells to form a large syncytium containing both eGFP and DiI signals together.

Figure 9A:
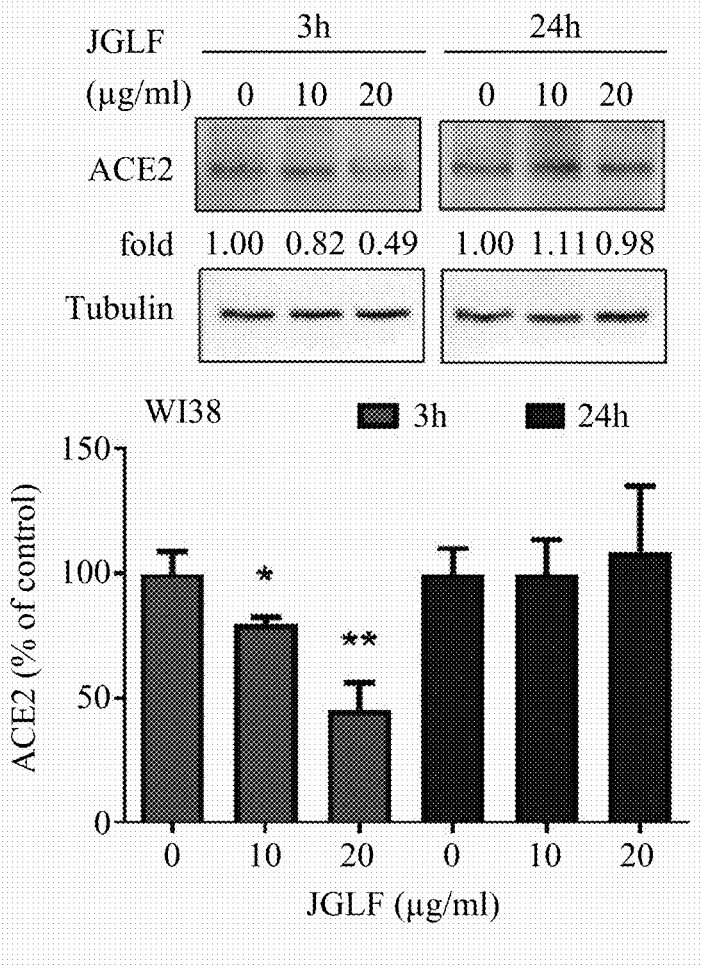
Figure 9B:
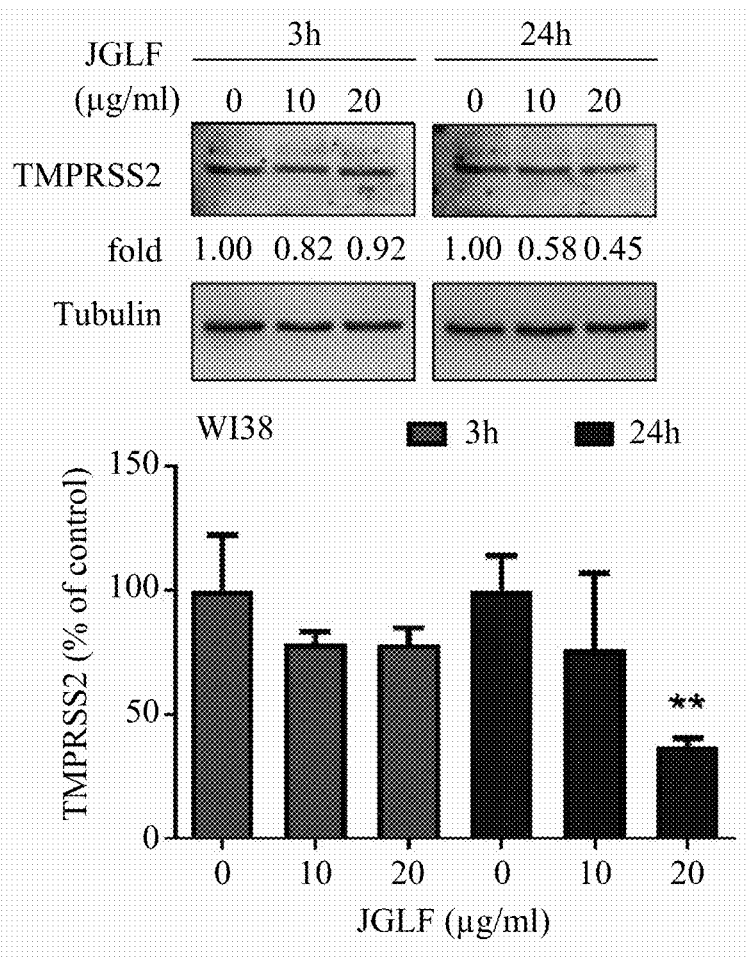
Figure 9C:
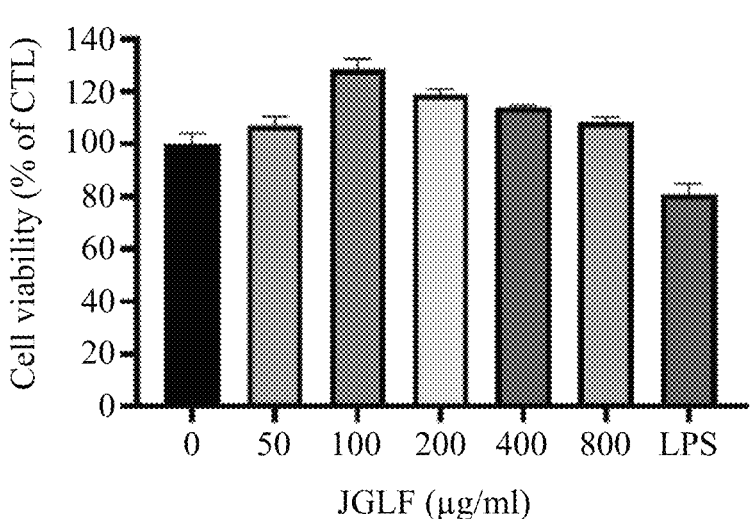
Figure 9D:
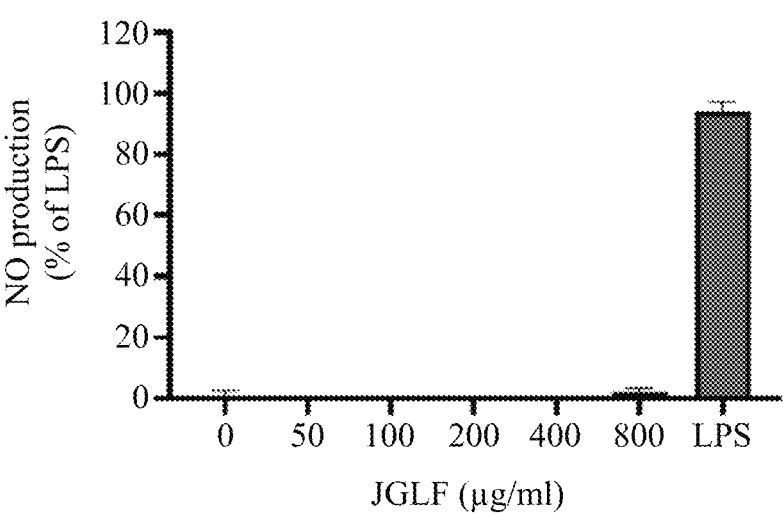
Figure 9E:
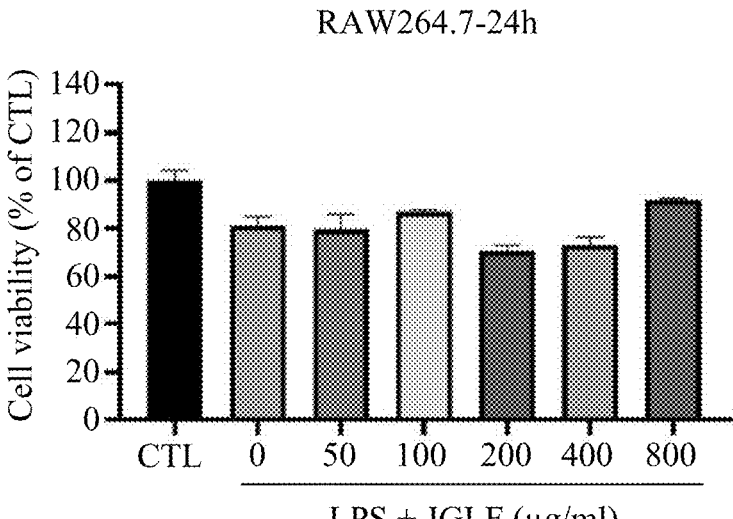
Figure 9F:
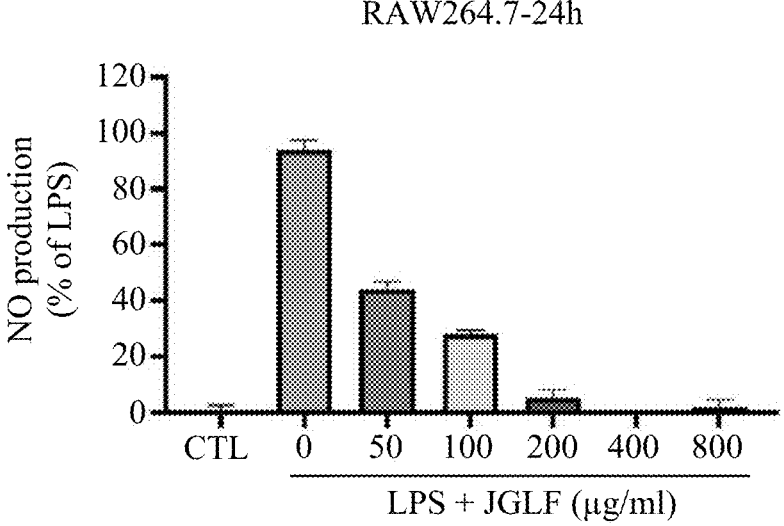
Figure 9G:
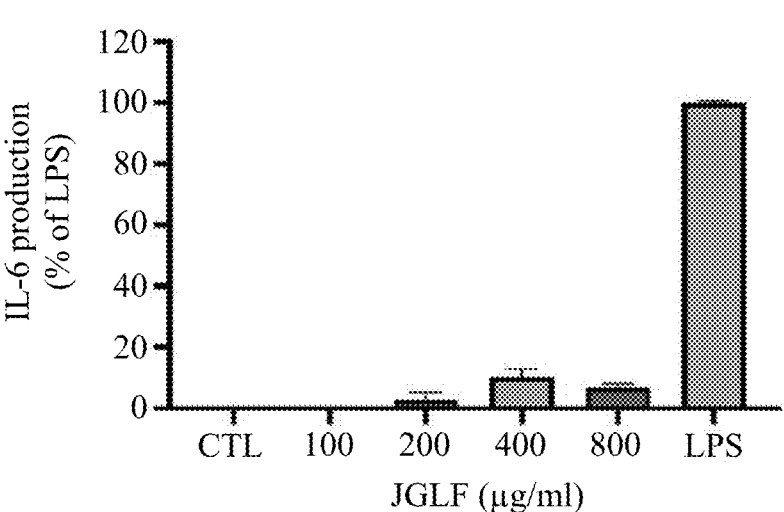
Figure 9H:
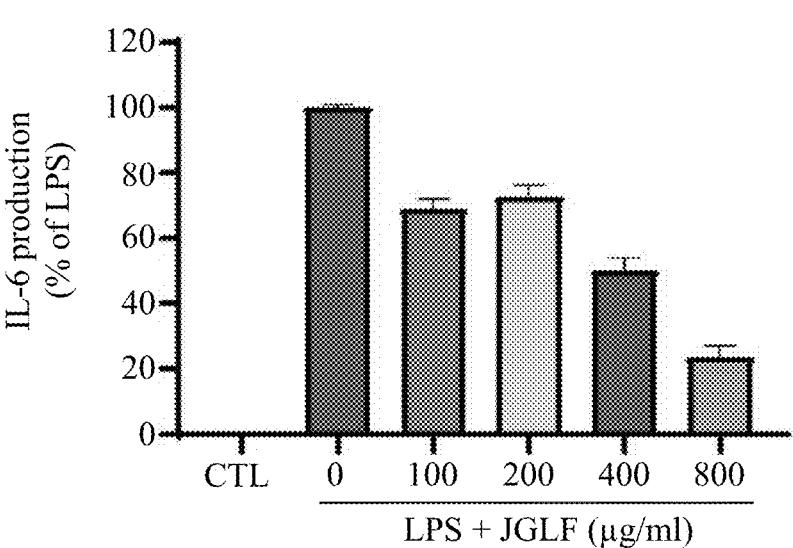

FIGS. 9A to 9H show effect of the herbal composition JGLF on the expressions of ACE2 and TMPRSS2, cell viability, NO production, and IL-6 production in different cell models. The data contains three independent experiments, and are presented as mean±SD, and error bars indicates SDs. Significant differences are indicated as * $p<0.05$,  $p<0.01$. FIGS. 9A and 9B show ACE2 and TMPRSS2 expression under JGLF treatment at different time points and doses, respectively. The expressions of ACE2 and TMPRSS2 were determined by Western blot. Tubulin was used as internal control. FIGS. 9C to 9F show the cell viability and NO production in RAW264.7 cells treated with or without LPS. RAW264.7 cells were treated with various concentrations of JGLF (0 to 800 µg/ml) or LPS (1 µg/ml) for 24 h. Cell viability and NO production were determined by MTT and Griess assay. Cell viability was normalized against control group and NO production was normalized against positive (LPS) group. FIGS. 9G and 9H** show the IL-6 production in RAW264.7 cells treated with or without LPS for 24 h. RAW264.7 cells were treated with various concentrations of JGLF (0 to 800 µg/ml) and/or LPS (1 µg/ml) for 24 h. IL-6 protein production was determined by ELISA and each group was normalized against positive (LPS alone) group.

Figure 9I:
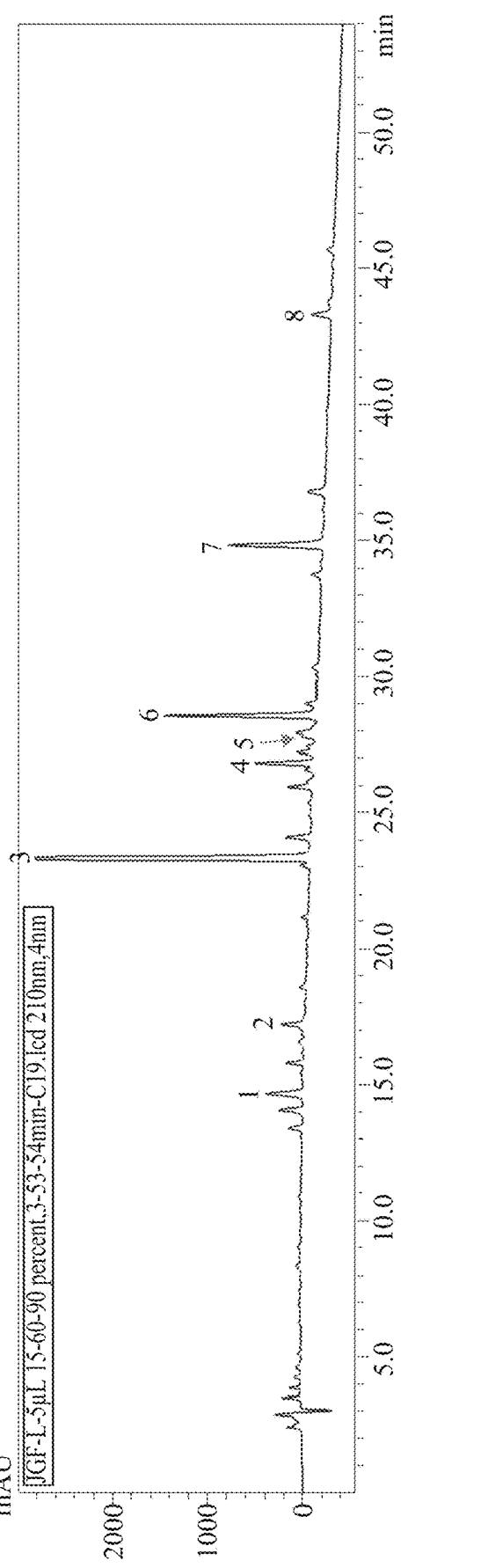

FIG. 9I shows the HPLC fingerprint of the herbal composition of the JGLF under UV 254 nm detection. Peak 1: forsythoside A, retention time (rt)=17.05 min; peak 2: specnuezhenide, rt=19.18 min; peak 3: baicalin, rt=24.43 min; peak 4: oroxyloside, rt=27.55 min; peak 5: acacetin-7-O-glucose, rt=31.21 min; peak 6: wogonoside, rt=29.37 min; peak 7: baicalein, rt=34.65; peak 8: wogonin, rt=42.24.

Figure 10A:
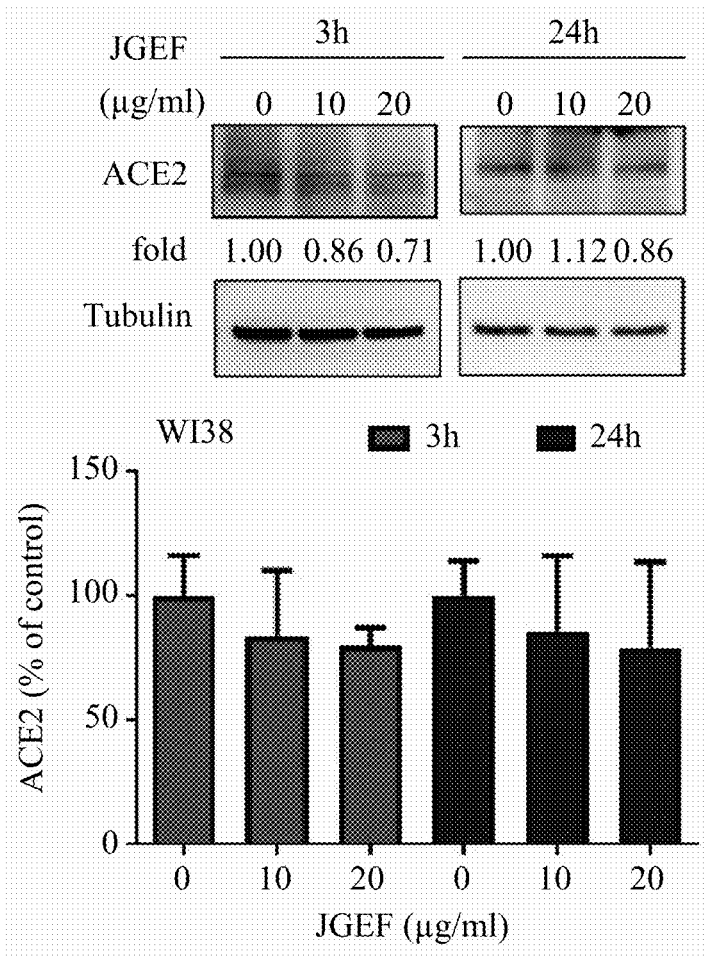
Figure 10B:
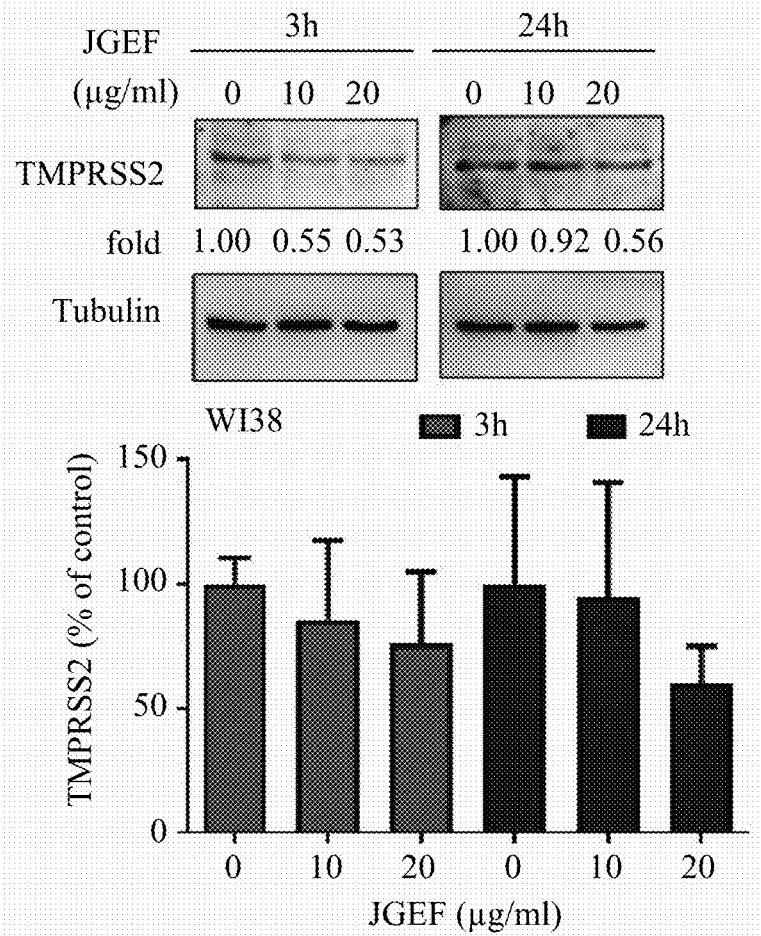
Figure 10C:
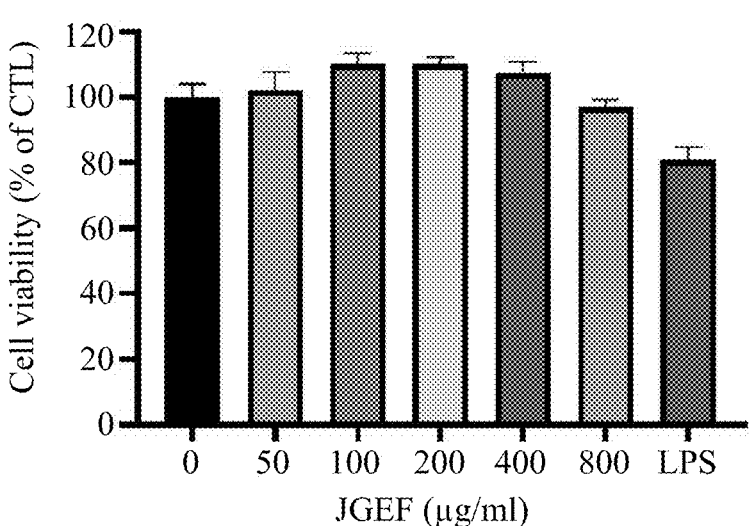
Figure 10D:
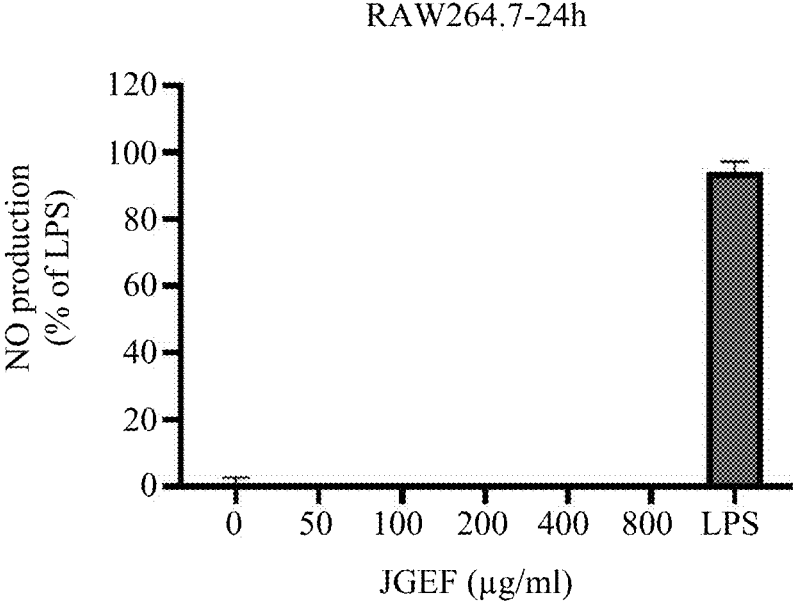

FIGS. 10A to 10H show the effect of the herbal compositions JGEF on the expressions of ACE2 and TMPRSS2, cell viability, NO production, and IL-6 production in different cell models. The data contains three independent experiments, and are presented as mean±SD, and error bars indicates SDs. FIGS. 10A and 10B show ACE2 and TMPRSS2 expression under JGEF treatment at different time points and doses, respectively, and TMPRSS2 expression in different times and doses after JGEF treatment. The expressions of ACE2 and TMPRSS2 were determined by Western blot. Tubulin was used as internal control. FIGS. 10C to 10F show the cell viability and NO production in RAW264.7 cells treated with or without LPS. RAW264.7 cells were treated with various concentrations of JGEF (0 to 800 µg/ml) or LPS (1 µg/ml) for 24 h. Cell viability and NO production were determined by MTT and Griess assay. Cell viability was normalized against control group and NO production was normalized against positive (LPS) group.

6

Figure 10E:
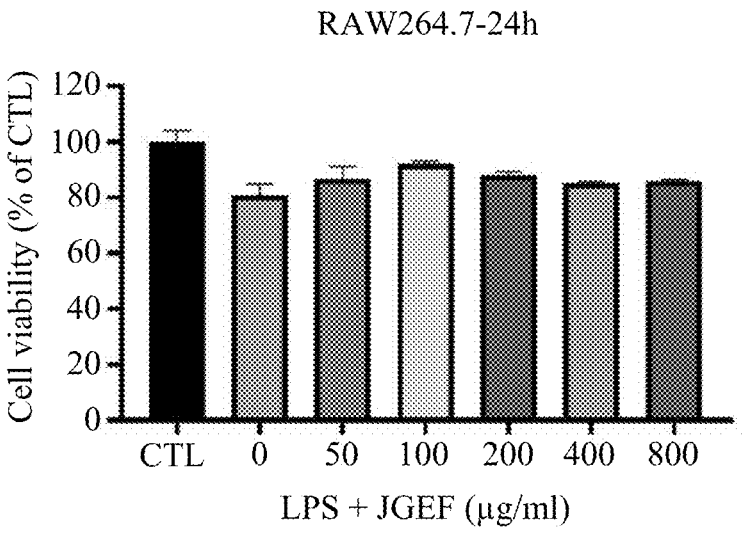
Figure 10F:
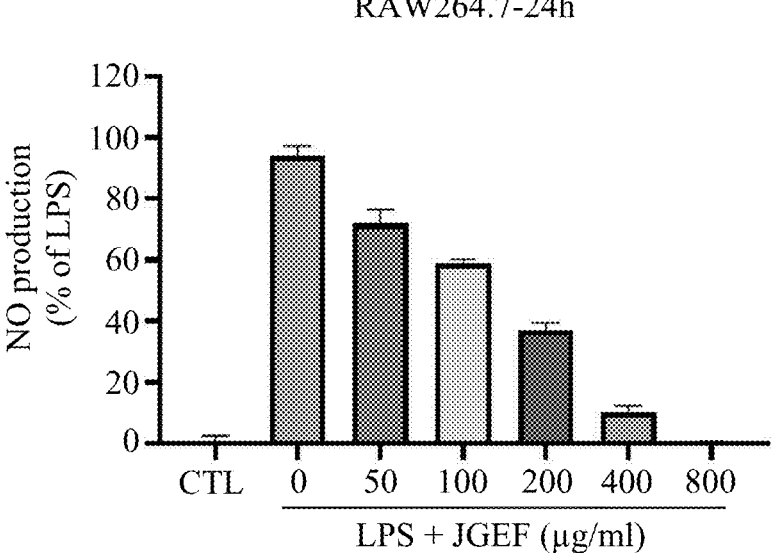
Figure 10G:
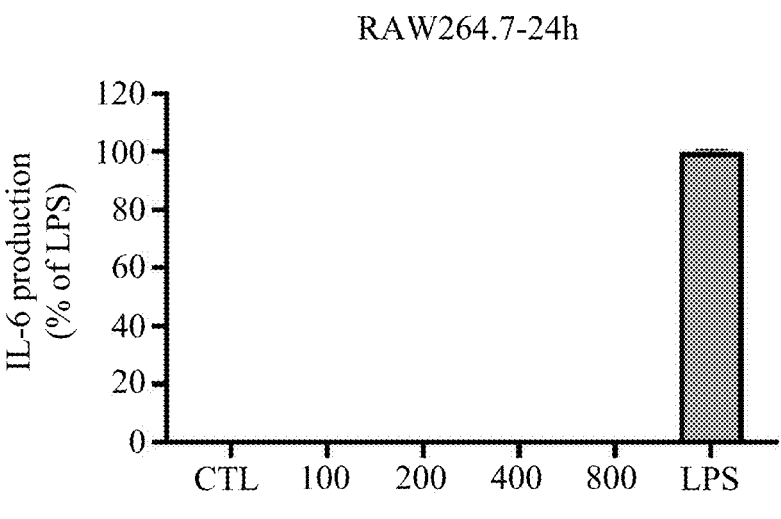
Figure 10H:
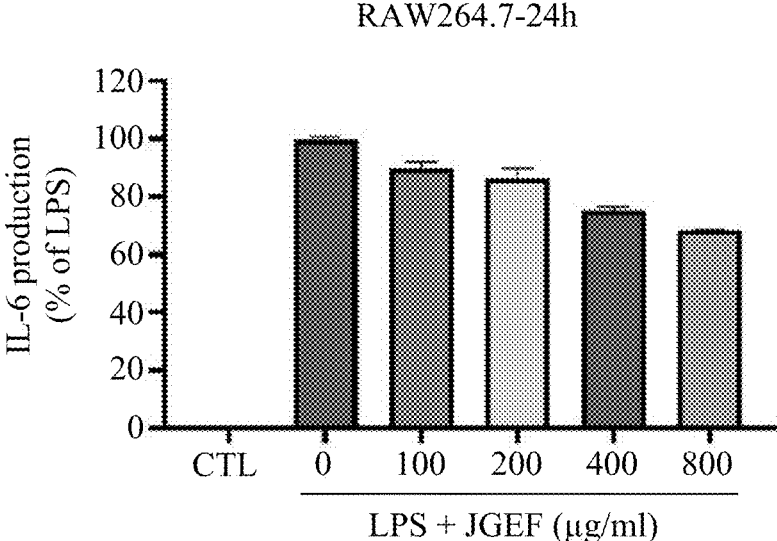

FIGS. 10G and 10H show the IL-6 production in RAW264.7 cells treated with or without LPS. RAW264.7 cells were treated with various concentrations of JGEF (0 to 800 µg/ml) and/or LPS (1 µg/ml) for 24 h. IL-6 protein production was determined by ELISA and each group was normalized against positive (LPS alone) group.

Figure 11A:
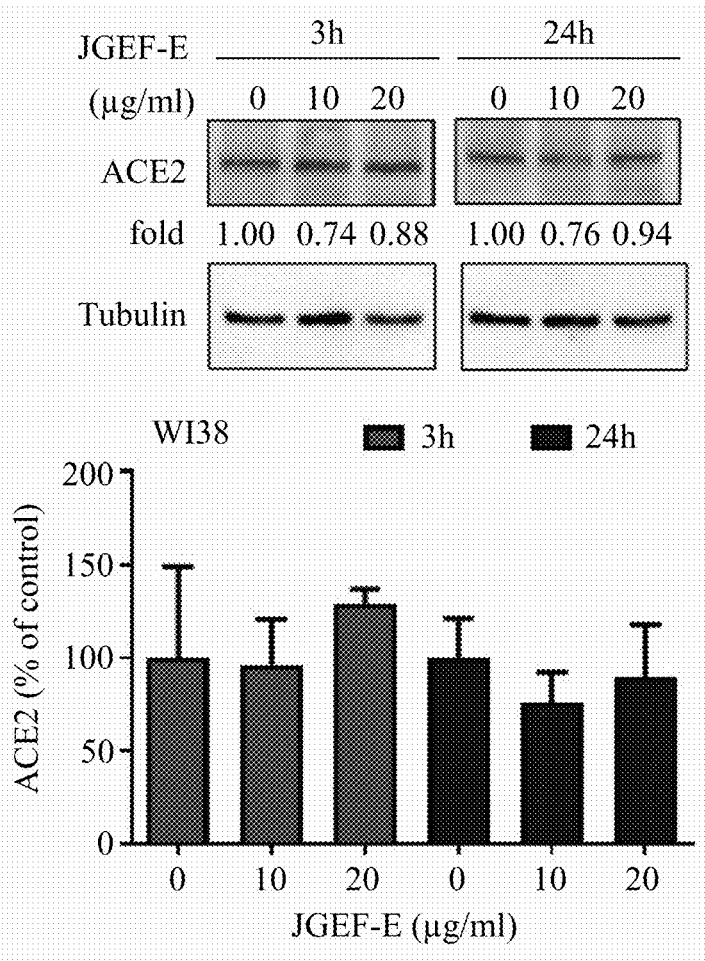
Figure 11B:
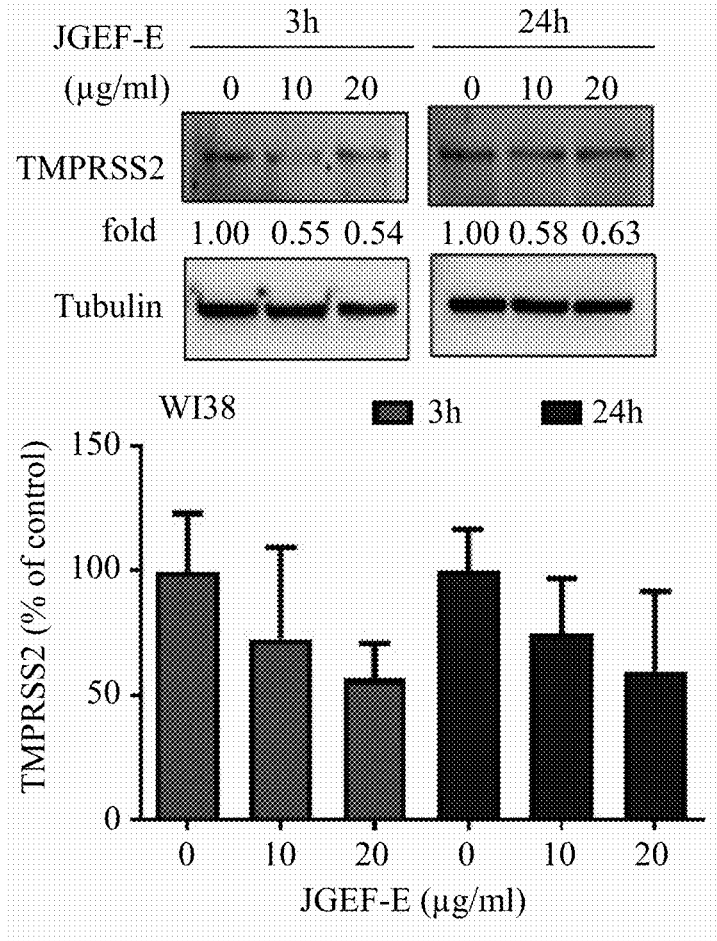

FIGS. 11A to 11F show effect of the herbal compositions JGEF-E on the expressions of ACE2 and TMPRSS2, cell viability, and NO production in different cell models. The data contains three independent experiments, and are presented as mean±SD, and error bars indicates SDs. FIGS. 11A and 11B show ACE2 expression and TMPRSS2 expression under JGEF-E treatment at different time points and doses, respectively. The expressions of ACE2 and TMPRSS2 were determined by Western blot. Tubulin was used as internal control. FIGS. 11C to 11F show the cell viability and NO production in RAW264.7 cells treated with or without LPS. RAW264.7 cells were treated with various concentrations of JGEF-E (0 to 200 µg/ml) or LPS (1 µg/ml) for 24 h. Cell viability and NO production were determined by MTT and Griess assay. Cell viability was normalized against control group and NO production was normalized against positive (LPS) group.

DETAILED DESCRIPTION OF THE EMBODIMENTS

The technical solutions illustrated in the examples of the present disclosure will now be described more clearly and completely, and it will be apparent that the described examples are merely part of the examples of the present disclosure and are not intended to be exhaustive. The present disclosure can also be implemented or applied as described in different examples. All other examples obtained without creative work by those skilled in the art are within the scope of the present disclosure.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

As used herein, the term "comprising" or "comprises" is used in reference to compositions, methods, and respective component(s) thereof, which are included in the present disclosure, yet open to the inclusion of unspecified elements or steps, whether essential or not.

The present disclosure is directed to an herbal composition, a method for preparing the herbal composition, and a method for preventing or treating a viral infection in a subject in need thereof by using the herbal composition.

In at least one embodiment, the viral infection prevented or treated by the method of the present disclosure may be caused by coronavirus (CoV). In at least one embodiment, the coronavirus is SARS-CoV or SARS-CoV-2.

In at least one embodiment, the viral infection leads to respiratory symptoms including sore throat, headache, cough, fever, rhinorrhea, diarrhea or new loss of taste or smell. In some embodiments, the viral infection also leads symptoms including fatigue, tension or pressure.

The structural proteins of CoVs including nucleocapsid (N), small envelope (E), matrix (M) and trimeric spike (S) glycoproteins, which are essential for virion assembly and function to complete the viral life cycle during infections. In some embodiments, the method for preventing or treating a viral infection of the present disclosure comprises administering to a subject in need thereof the herbal composition that induces degradation of angiotensin-converting enzyme 2 (ACE2) receptor, thereby blocking the interaction of the coronavirus S-protein and host cells, as well as suppressing the expression of proteins that are necessary for entry and/or replication of the coronavirus in a host, such as transmembrane serine protease 2 (TMPRSS2), thereby influencing the risk of contracting the viral infection or aggravating the disease progression. Accordingly, the herbal composition of the present disclosure may have antiviral activity and be useful for effectively preventing or treating viral infections.

As used herein, the term "preventing" or "prevention" refers to preventive or avoidance measures for a disease or symptoms or conditions of a disease, which include, but are not limited to, applying or administering one or more active agents to a subject who has not yet been diagnosed as a patient suffering from the disease or the symptoms or conditions of the disease but may be susceptible or prone to the disease. The preventive measures of the present disclosure are provided to avoid, prevent, or postpone the occurrence of the disease or the symptoms or conditions of the disease.

As used herein, the term "treating" or "treatment" refers to obtaining a desired pharmacologic and/or physiologic effect, e.g., inhibition of viral entry and/or replication in a host. The effect may be prophylactic in terms of completely or partially preventing a disease or symptoms or conditions thereof, or may be therapeutic in terms of completely or partially curing, alleviating, relieving, remedying, or ameliorating a disease or an adverse effect attributable to the disease or symptoms or conditions thereof.

As used herein, the terms "patient" and "subject" are used interchangeably. The term "subject" means a human or animal. Examples of the subject include, but are not limited to, human, monkey, mice, rat, woodchuck, ferret, rabbit, hamster, cow, horse, pig, deer, dog, cat, fox, wolf, chicken, emu, ostrich, and fish. In some embodiments of the present disclosure, the subject is a mammal, e.g., a primate such as a human.

As used herein, the phrase "an effective amount" refers to the amount of an active agent that is required to confer a desired preventive or therapeutic effect on a subject in need thereof (e.g., reducing the number of viruses in a host). Effective doses may vary, as recognized by those skilled in the art, depending on routes of administration, excipient usage, the possibility of co-usage with other therapeutic treatment, and the condition to be treated.

As used herein, the term "administering" or "administration" refers to the placement of an active agent into a subject by a method or route which results in at least partial localization of the active agent at a desired site to produce the desired effect. The active agent described herein may be administered by any appropriate route known in the art. For example, the herbal composition of the present disclosure is administered to the subject by oral administration.

In at least one embodiment, the herbal composition of the present disclosure comprises a decoction of a combination of herbs and a pharmaceutically acceptable carrier thereof, wherein the combination of herbs comprises at least five of *Forsythia suspensa, Scutellaria baicalensis, Bupleurum Chinese, Magnolia officinalis, Agastache rugosa, Astragalus membranaceus, Atractylodes macrocephala* and seeds of *Ligustrum lucidum.*

In at least one embodiment, the herb combination comprises 25% to 35% (e.g., 25%, 26%, 27%, 28%, 29%, 30%, 31%, 32%, 33%, 34% and 35%) by weight of *Forsythia suspensa*, 18% to 26% (e.g., 18%, 19%, 20%, 21%, 22%, 23%, 24%, 25% and 26%) by weight of *Scutellaria baicalensis*, 15% to 25% (e.g., 15%, 16%, 17%, 18%, 19%, 20%, 21%, 22%, 23%, 24%, and 25%) by weight of *Bupleurum Chinese*, 15% to 25% (e.g., 15%, 16%, 17%, 18%, 19%, 20%, 21%, 22%, 23%, 24%, and 25%) by weight of *Magnolia officinalis*, 7% to 15% (e.g., 7%, 8%, 9%, 10%, 11%, 12%, 13%, 14%, and 15%) by weight of *Agastache rugosa*, 25% to 35% (e.g., 25%, 26%, 27%, 28%, 29%, 30%, 31%, 32%, 33%, 34% and 35%) by weight of *Astragalus membranaceus*, 7% to 15% (e.g., 7%, 8%, 9%, 10%, 11%, 12%, 13%, 14%, and 15%) by weight of seeds of *Ligustrum lucidum* and 7% to 15% (e.g., 7%, 8%, 9%, 10%, 11%, 12%, 13%, 14%, and 15%) by weight of *Atractylodes macrocephala*, based on a total weight of the herbal raw material.

In at least one embodiment, the pharmaceutically acceptable carrier in the herbal composition may be diluents, disintegrants, binders, lubricants, glidants, surfactants, or any combination thereof. The carrier in the composition is "acceptable" in the sense that it is compatible with the active agent of the composition (e.g., capable of stabilizing the active agent) and not deleterious to the subject to be administered. One or more solubilizing agents may be utilized as pharmaceutical excipients for delivery of an active ingredient. Examples of other carriers include colloidal silicon oxide, magnesium stearate, cellulose, and sodium lauryl sulfate. In some embodiments, the herbal composition comprises a pharmaceutically acceptable carrier selected from water, ethanol, maltodextrin, crystalline cellulose, and any combination thereof.

Many examples have been used to illustrate the present disclosure. The examples below should not be taken as a limit to the scope of the present disclosure.

EXAMPLES

For a more detailed description of the present disclosure, the herbal composition, the preparation method thereof and the use of the composition will be provided and described in detail with reference to the following examples. The materials used in the present disclosure but unannotated herein are commercially available.

Preparation Example 1

The herbal composition of the JGF uses five herbs: 10 mg of Lianqiao (*Forsythia suspensa*) (30.3% of total weight), 8 mg of Huangqin (*Scutellaria baicalensis*) (24.2% of total weight), 6 mg of Chaihu (*Bupleurum Chinese*) (18.2% of total weight), 6 mg of Houpo (*Magnolia officinalis*) (18.2% of total weight) and 3 mg of Huoxiang (*Agastache rugosa*) (9.0% of total weight).

The herbal composition of the JGLF contains Huangqin (*Scutellaria baicalensis*) (3~9 g), Lianqiao (*Forsythia suspensa*) (3~9 g), Huangqi (*Astragalus membranaceus*) (3~9 g), Chaihu (*Bupleurum Chinese*) (3~9 g), Huoxiang (*Agastache rugosa*) (2~5 g), Nvzhenzi (seeds of *Ligustrum lucidum*) (2~5 g).

The herbal composition of the JGEF contains Huangqin (*Scutellaria baicalensis*) (3~9 g), Lianqiao (*Forsythia suspensa*) (3~9 g), Huangqi (*Astragalus membranaceus*) (3~9 g), Chaihu (*Bupleurum Chinese*) (3~9 g), Huoxiang (*Agastache rugosa*) (2~5 g), Houpo (*Magnolia officinalis*) (2~5 g), Nvzhenzi (seeds of *Ligustrum lucidum*) (2~5 g), Baizhu (*Atractylodes macrocephala*) (2~5 g).

All ingredients were purchased from a certificated pharmaceutical company (KO DA Pharmaceutical Co., Ltd., Taiwan). JGF is produced by the Branch of Linsen Chinese & Kunming, Taipei City Hospital (Taipei, Taiwan).

Herbs for JGF, JGLF, and JGEF were soaked in water and subsequently boiled for 4 hours using an automatic herb boiling machine at atmospheric pressure, that is, the pressure of 1 atm. The final product is 110 g/pack in weight and 100 mL/pack in volume. HPLC was performed to ensure the quality and standard contents of JGF and JGLF, as shown in FIGS. 7 and 9I.

Preparation Example 2

30 wt % of *Forsythia suspensa,* 24 wt % of *Scutellaria baicalensis,* 18 wt % of *Bupleurum Chinese,* 18 wt % of *Magnolia officinalis* and 9 wt % of *Agastache rugosa* were soaked in water in an herbal weight to water volume ratio of 1:1, and subsequently boiled for 2 hours under pressure of 1.2 atm. The final product is 110 g/pack in weight and 100 mL/pack in volume.

Preparation Example 3

24 wt % of *Forsythia suspensa,* 24 wt % of *Scutellaria baicalensis,* 18 wt % of *Bupleurum Chinese,* 9 wt % of *Magnolia* officinalis, 9 wt % of *Agastache* rugosa, 9 wt % of *Astragalus membranaceus,* 9 wt % of seeds of *Ligustrum lucidum* and 27 wt % of *Atractylodes macrocephala* were soaked in water in an herbal weight to water volume ratio of 1:5, and subsequently boiled for 4 hours under 1.5 atmospheric pressure. The final product is 110 g/pack in weight and 100 mL/pack in volume.

Preparation Example 4

JGEF or JGLF described in Preparation Example 1 was soaked in water in an herbal weight to water volume ratio of 1:5, and subsequently boiled for 4 hours under 1.5 atmospheric pressure. The final product is 110 g/pack in weight and 100 mL/pack in volume.

Preparation Example 5

In this example, an ethanol extract was prepared with the amount of herbs described in Preparation Example 2 or 3, except that the herbs were soaked in 95% alcohol in a weight to alcohol volume ratio of 1:1 and incubated for 3 days to obtain an ethanol extract from the herbal composition.

Preparation Example 6

In this example, an ethanol extract was prepared with the amount of herbs JGEF described above. Dry weight of herbs for JGEF-E were measured after drying and soaked in cold 95% ethanol. 200 ml of 95% ethanol was added to the of 40 g (in dry weight) of JGEF-E herbs. The mixture was shake with sonicate for 30 minutes and filtered out. The extraction solution was keep for storage. Repeat the second and third steps until the ethanol is not colored (5 times for this extraction). Extract was subject to a suction filter followed by an oven to remove ethanol. The rest solution was lyophilized. Weight the final product and re-dissolve it into 160 mg/ml with DMSO for subsequent experiments.

Pharmacological Example 1: Materials and Methods

The therapeutic effect of the herbal composition provided in the present disclosure for the prevention or treatment of coronavirus infection was determined in the following Pharmacological Examples 2 to 8. The experimental methods used in these examples were described as follows.

Clinical Setting and Participants

JGF was administered to the front-line staff in a hospital as a preventative measure against COVID-19. The composition was then provided to another five public hospitals in the Taipei area. The clinical study was conducted from Feb. 20, 2020 to May 20, 2020. JGF was taken by subjects as a complementary preventative strategy. Non-symptomatic subjects were advised to take one dose a week, and those who displayed COVID-19-like symptoms were advised to take two doses a week.

A total of 2,468 packs of JGF were provided to 1,086 individuals, of which 396 individuals participated in the questionnaire. All participants were from the Taipei area (Taipei city and New Taipei city). The protocol was approved by the Taipei City Hospital Institutional Review Board (TCHIRB-10904015). The participants were then asked to fill out the online questionnaire voluntarily or in person at the hospitals. The questionnaire recorded an individual's demographic information, symptoms prior to taking JFG and any improvement in symptoms or adverse effects and satisfaction.

Cell Culture and Virus

BHK-21 cells and Calu-3 cells were cultured in Dulbecco's Modified Eagle Medium (DMEM, Gibco) supplemented with 10% fetal bovine serum (FBS) and 1× penicillin/streptomycin solution. Vero E6 cells were maintained in high glucose DMEM (GeneDireX) supplemented with 10% FBS. Normal human lung epithelial WI-38 VA-13 subline 2RA and fibroblast MRC-5 cells were purchased from the Bioresource Collection and Research Center (BCRC, Hsinchu, Taiwan). Cells were cultured in minimum essential medium (Eagle, Gibco) supplemented with 10% FBS, 2 mM L-glutamine, 1.5 g/L sodium bicarbonate, 0.1 mM non-essential amino acids, and 1.0 mM sodium pyruvate at 37° C. under a mixture of 95% air and 5% $CO_2$.

SARS-CoV-2 strain 3586 (TSGH_15 GISAID accession number EPI_ISL_436100) was isolated at the Institute of Preventive Medicine, National Defense Medical Center and amplified in Vero E6 cells. The viral titer was determined using a plaque assay. SARS-CoV-2 was handled in a BSL-3 laboratory.

Cell-Cell Fusion Assay

Calu-3, as target cells, were seeded in a 12-well plate ($1×10^6$ per well) and formed a single-layer of cell films for 48 h. BHK-21 cells were seeded in a 6-well plate ($4×10^5$ per well) and transfected with both enhanced green fluorescent protein (GFP) and spike plasmids at a ratio of 1:5 for 24 h. GFP/spike co-expressing BHK-21 cells were harvested using cell dissociation buffer (Gibco) and resuspended in serum free DMEM. For spike-mediated cell-cell fusion assays, GFP/spike co-expressing BHK-21 cells, as donor cells, were added to Calu-3 cells and incubated at 4° C. for 45 minutes to allow cell-cell binding. They were then washed with PBS. The growth medium was replaced, and the cells were then incubated at 37° C. for 4 h to allow cell-cell fusion. After incubation, five fields were randomly selected in each well to record the GFP-expressing cell images using an inverted fluorescence microscope (Olympus IX70). The extension area of the GFP-expressing cell images was quantified to determine the degree of cell-cell fusion using ImageJ software. The fold-change in the EGFP-positive area of the control group from 0 h to 4 h was used as a basis to gauge the fold change in the two experimental conditions. As shown in the following formula, if the relative area change of GFP was smaller than that of the control group, the normalized percentage would be smaller than 100%, indicating an effective inhibition of the JGF. On the other hand, if the relative area change of GFP was equal to or even greater than that of the control group, the normalized percentage would be approximately equal to or greater than 100%, which would in turn indicate the inhibition to be ineffective.

The normalized percentage (%)=(the fold change of
GFP area)/(the fold change of GFP area in con-
trol)×100

SARS-CoV-2 Plaque Formation Assay

Vero E6 cells ($4×10^5$/well) were seeded into 12-well plates. Before infection with SARS-CoV-2 strain 3586, cells were treated with JGF (50, 100 and 200 µg/mL) for 3 h at 37° C. and 5% $CO_2$ and were shaken occasionally. Following the JGF treatment, 50 µL SARS-CoV-2 ($2×10^3$ plaque-forming unit (PFU)/well) samples were added and adsorbed for 1 h at 37° C. After the absorption period, the medium was removed, and 4 mL of 1.55% (v/v) methylcellulose in DMEM (2% FBS added) with JGF was added for 3 days at a temperature of 37° C. in 5% $CO_2$. Cells were then fixed with 10% formaldehyde for 1 h at room temperature, and 0.5% (w/v) crystal violet was added into the fixed cells for at least 30 min at room temperature. SARS-CoV-2 virus (nCoV-19/Taiwan/4/2020) was obtained from the Taiwan Centers of Disease Control (CDC). All experiments involving live SARS-CoV-2 were performed in CDC-approved BSL-3 and BSL-4 facilities at the Institute of Preventive Medicine in the National Defense Medical Center in accordance with requirements of the institutional biosafety committee.

Cell Viability Assay

Cells ($5×10^4$ cells/well) were seeded into 12-well culture plate dishes and incubated overnight. Cells were then treated with JGF (0 to 800 µg/mL) for 48 and 72 h. After incubation, each well was rinsed with PBS, and cells that attached to the bottom of the well were fixed and stained with 1% crystal violet solution or (3-(4,5-dimethylthiazol-2-yl)-2,5-diphe-nyltetrazolium bromide) (MTT) solution, as described in T. Y. Lin, H. Y. Hsu, W. H. Sun, T. H. Wu, and S. M. Tsao, "Induction of Cbl-dependent epidermal growth factor receptor degradation in Ling Zhi-8 suppressed lung cancer," Int. J. Cancer 140 (2017) 2596-2607.

Lactate Dehydrogenase (LDH) Assay to Detect Cytotoxicity for JGF in BHK-21 and Calu-3 Cells The cytotoxicity of JGF on BHK-21 and Calu-3 cells was determined using cytotoxicity detection KitPLUS (LDH; Merck). BHK-21 and Calu-3 cells were seeded in 96-well plates ($1×10^4$ cells/well). After incubation overnight at 37° C., the cells were replaced into growth medium containing various concentrations of JGF (20, 40, and 80 µg/mL), and incubated at 37° C. for 24 h. The untreated cells were the low control so that they spontaneously release LDH in normal condition. Cells that were treated with lysis buffer (5 µL) for 15 min were the high control and were used to determine the maximum release of LDH in the cells. To determine the LDH activity, 100 µL of reaction mixture (freshly prepared by mixing catalyst and dye solution) was added to each well and incubated for 15 min at room temperature. Multimode microplate readers (TECAN SPARK) were used to measure the absorbance of the samples at a wavelength of 490 nm. The percentage of cytotoxicity was determined from 3 independent experiments and the cytotoxicity was determined by the following equation:

Cytotoxicity (%)=(the absorbance of JGF-treated
group–the absorbance of no treatment group)/

(the absorbance of triton-treated group–the
absorbance of no treatment group)×100

Sample Preparation for Western Blotting Analysis

Cells were rinsed with cold PBS containing 1% $Na_3VO_4$ and harvested by scraping the cells into proteinase inhibitors and a phosphatase inhibitor cocktail (Sigma Chemical Co.) containing lysis buffer (10 mM HEPES (pH 7.9), 10 mM KCl, 0.1 mM EDTA, and 0.1 mM EGTA). Whole cell lysates were centrifuged for 13,000×g for 10 min at 4° C. The supernatant was collected as the cell extracts. The concentration of the protein from cell lysate was determined using a Bradford assay (Bio-Rad, Hercules, CA). The cell lysate samples (30 µg) were then subjected to Western blotting analysis. The expression of 3-actin was used as an internal control. The procedures for the Western blotting assay used in the present disclosure are commonly known in the field. Antibodies against ACE2, TMPRSS2 and actin were purchased from GeneTex (Hsinchu, Taiwan).

RNA Extraction and Quantitative Polymerase Chain Reaction (q-PCR)

Total RNA was isolated from cells using TRIzol reagent (Invitrogen, Carlsbad, CA, USA). The cDNA synthesis was performed by using a HiScript II 1st Strand cDNA Synthesis Kit (Vazyme, J S, China). The q-PCR was carried out by using a Fast SYBR Green Master Mix (Thermo Fisher Scientific) in triplicate and an Applied Biosystems Model 7000 instrument (Thermo Fisher Scientific). The data were quantitated using $2^{-\Delta Ct}$ ($\Delta Ct=Ct_{target\ gene}-Ct_{GAPDH}$; Ct: cycle number when the fluorescent value of the sample is equal to the threshold value). Primer sequences for this study include hTMPRSS2-F: 5'-CCTCTAACTGGTGT-GATGGCGT-3' (SEQ ID NO.: 1); hTMPRSS2-R: 5'-TGCCAGGACTTCCTCTGAGATG-3' (SEQ ID NO.: 2). hGAPDH-F: 5'-TGGTATCGTGGAAGGACTCA-3' (SEQ ID NO.: 3); and hGAPDH-R: 5'-AGTGGGTGTCGCTGTT-GAAG-3' (SEQ ID NO.: 4).

Animal Model

Six- to eight-month-old male C57BL/6 mice were purchased from the National Laboratory Animal Center (Taipei, Taiwan). To determine the effect of JGF on the expression of ACE2 and TMPRSS2 in various organs of mice, the mice were randomly sorted into experimental groups (n=3). For Experiment 1, mice were fed with JGF (8 mg/mouse/day) twice. For Experiment 2, JGF was filled in a closed space using a low-temperature steam method (30 to 32 degrees) and inhaled by mice. After exposure to JGF for 30 minutes, mice were moved to a normal environment for ten minutes and then underwent another 30 minutes of exposure. Mice were sacrificed after receiving JGF for 3 h. All procedures were approved by and performed in accordance with the guidelines and regulations of the Institutional Animal Care and Use Committee (IACUC) of National Yang Ming Chiao Tung University (IACUC Approval No.: 1100511).

Statistical Analysis

Statistical differences between the experimental groups were determined using a t-test in GraphPad Prism8. A vale of $P<0.05$ indicates a statistically significant result. The experiments were conducted three times or as indicated, and all data are expressed as mean±standard deviation (SD).

Pharmacological Example 2: Clinical Observation
of Human Subjects Treated by JGF The clinical observations involved 396 subjects receiving JGF and participated in the questionnaire. The average age of the participants was 45.9 years old, with a standard deviation of 14.1 years. The ratio of males to females is 35.1% (male) and 64.9% (female). Table 1 below summarizes the demographic and clinical characteristics for the 396 subjects who participated in the questionnaire.

It was found that sore throat was the most reported COVID-19-like symptom, with 34 subjects displaying the symptom. Cough and headache are the second and third most commonly reported COVID-19-like symptoms and a loss of taste and smell (dysgeusia) is the least commonly reported COVID-19-like symptoms. Non-COVID-19-like symptoms that were reported include fatigue (n=128) and tension (n=102).

Seven days after taking JGF, 91.2% of subjects who experienced a sore throat reported that the symptoms had improved. Improvements in non-COVID-19-like symptoms, such as fatigue (81.3%) and tension (68.6%), were also reported.

TABLE 1

| Demographic and clinical characteristics of the subjects with COVID-19-like symptoms | | |
|---|---|---|
| Basic data | All (n = 396) | |
| Age, years (SD) | 45.9 (14.1) | |
| Male % | 35.1 | |
| Female % | 64.9 | |
| | Subjects displaying symptoms, persons (%) | Rate of improvement, persons/ all persons (%) |
| COVID-19-like symptoms | | |
| Sore throat | 34 (8.6) | 31/34 (91.2) |
| Headache | 25 (6.3) | 19/25 (76.0) |
| Cough | 29 (7.3) | 23/29 (79.3) |
| Fever | 13 (3.3) | 11/13 (84.6) |
| Rhinorrhea | 23 (5.8) | 18/23 (78.2) |
| Diarrhea | 24 (6.1) | 18/24 (75.0) |
| New loss of taste or smell | 3 (0.8) | 1/3 (33.3) |
| Associated main symptoms | | |
| Fatigue | 128 (32.3) | 104/128 (81.3) |
| Tension and pressure | 102 (25.8) | 70/102 (68.6) |

Pharmacological Example 3: JGF Prevents Membrane Fusion and the Formation of Syncytium S protein of SARS-CoV-2 present on a cellular membrane triggers the formation of receptor-dependent syncytia, and a fluorescence-based cell-cell fusion assay is adopted to examine the formation of membrane fusion between cells expressing SARS-CoV-2. For example, BHK-21 cells are made to express both SARS-CoV-2 S protein and enhanced green fluorescent protein (GFP) and act as the effectors, while Calu-3 cells express endogenous hACE2 and act as the target cells.

Figure 1A:
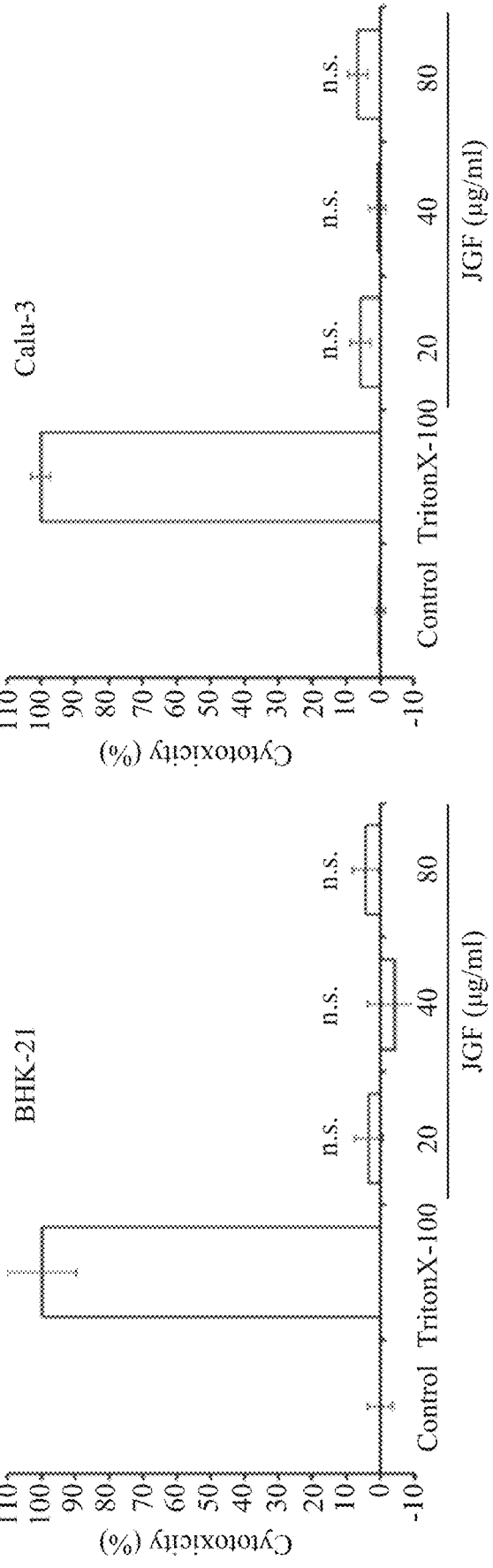
FIGS. 1A to 1D illustrate the inhibitory activity of the herbal compositions of the present disclosure on the interactions between SARS-CoV-2 spike (S) protein and ACE2 receptor.

For this assay, the binding of BHK-21 cells with Calu-3 cells indicates that SARS-CoV-2 S protein binds with the ACE2 receptor and the formation of syncytium is the result of membrane fusion. To confirm the cytotoxicity of JGF to BHK-21 and Calu-3 cells, cells were treated with various concentrations from 20 to 80 μg/mL of JGF. The treatment of Triton-100 was used as a positive control. Compared to the control group which received no JGF treatment, LDH assay depicted that JGF caused no significant amount of cell death, suggesting that JGF is not cytotoxic to either BHK-21 cells or Calu-3 cells, as shown in FIG. 1A.

Figure 1B:
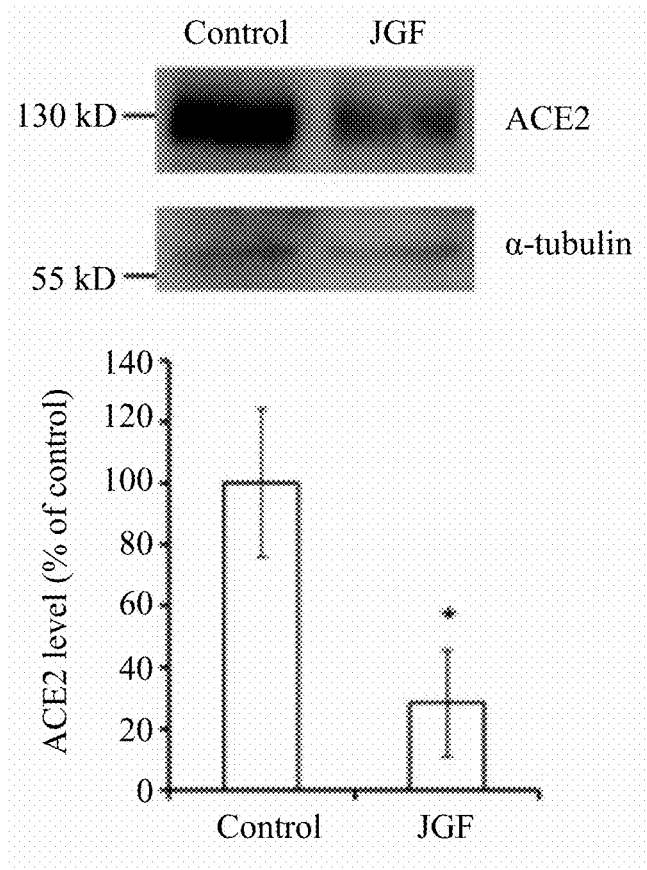

The effect of JGF on the expression of the ACE2 in Calu-3 cells was then determined by Western blotting assay. The results showed that the level of the ACE2 was significantly decreased, for approximately 70% in the presence of 40 μg/mL of JGF treatment, as shown in FIG. 1B.

Given that the occurrence of cell-cell fusion can be visualized as syncytium formation in the cell-cell fusion experiment, the results of confocal microscopy imaging revealed that, as shown in FIG. 8, only in the presence of the SARS-CoV-2 S protein, DiI-labeled cellular compartments of Calu-3 cells were co-localized with GFP signals within large syncytium, suggesting the fusion of GFP-expressing BHK-21 cells with DiI-labeled Calu-3 cells.

Figure 1C:
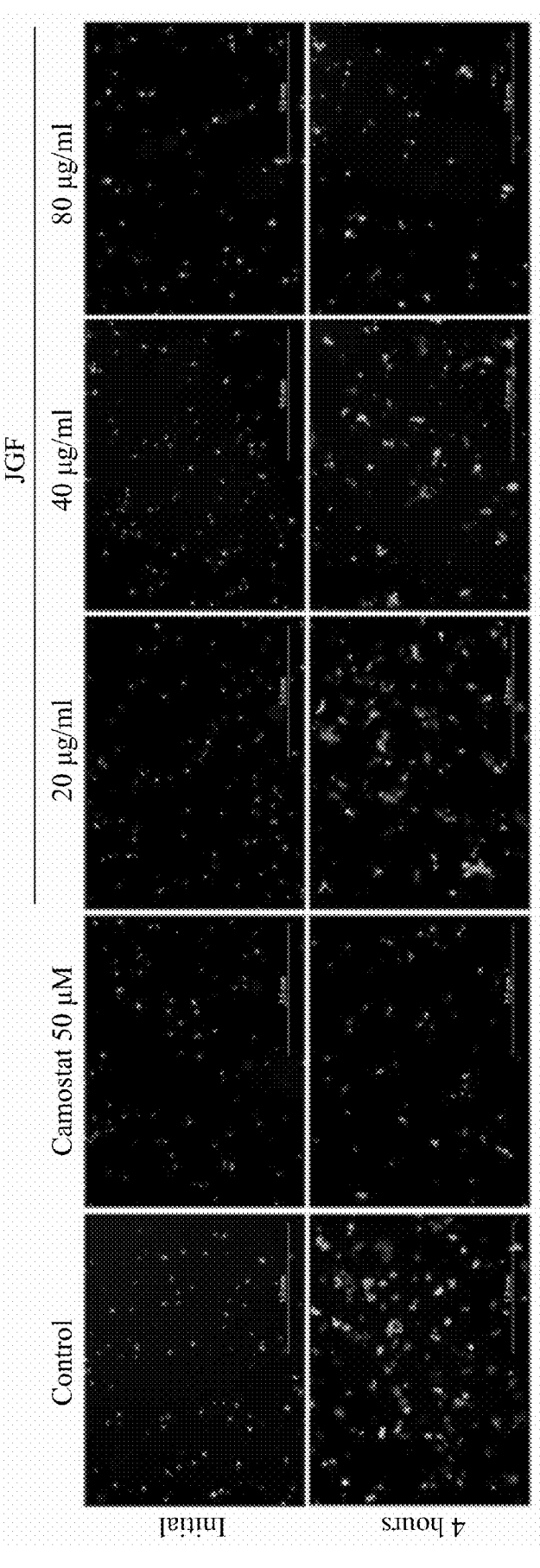
Figure 1D:
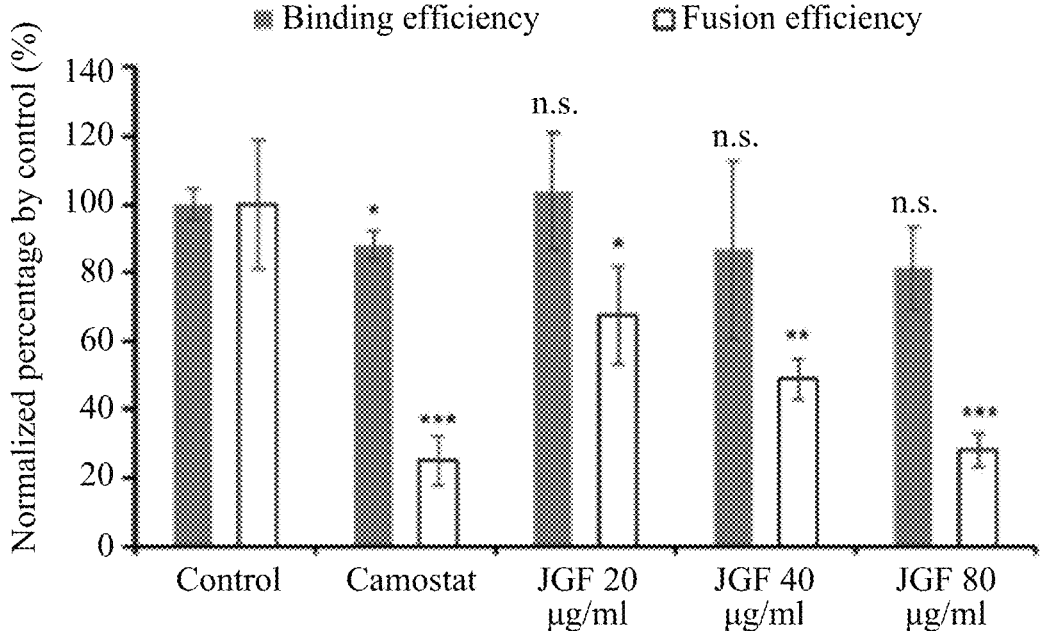

In the cell-cell fusion assay, the fluorescence microscopy imaging revealed that the treatment of JGF inhibits the formation of syncytium, as shown in FIGS. 1C and 1D. The treatment of the camostat, which is a pharmacological inhibitor of TMPRSS2 protease, as shown in FIGS. 1C and 1D, resulted in the inhibition of syncytium formation and was used as a positive control group. Also shown was that the inhibition of JGF showed a dose-dependent manner, suggesting that JGF can specifically interrupt SARS-CoV-2 S-mediated membrane fusion. These results suggest that JGF can be used as an anti-SARS-CoV-2 agent because it suppresses membrane fusion, which is one of the first steps of viral infection.

Figure 2A:
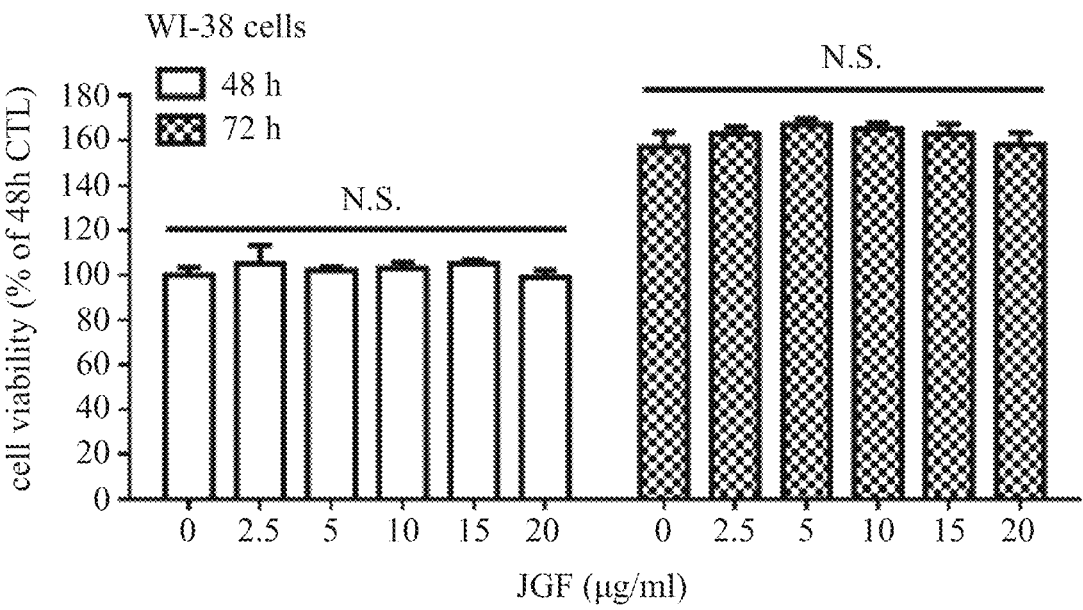
FIGS. 2A and 2B illustrate the bar graphs of the effect of the herbal compositions of the JGF on the cell viability of lung fibroblast WI-38 and MRC-5 cells, respectively. Cells were treated with various low concentrations of JGF (0 to 20 μg/mL) for 48 and 72 h. Each group of JGF-treated samples was normalized against an untreated control (CTL). Cell viability was determined using a crystal violet assay. Data were representative of three separated experiments and were presented as the mean±SD; error bars indicated SDs.
Figure 2B:
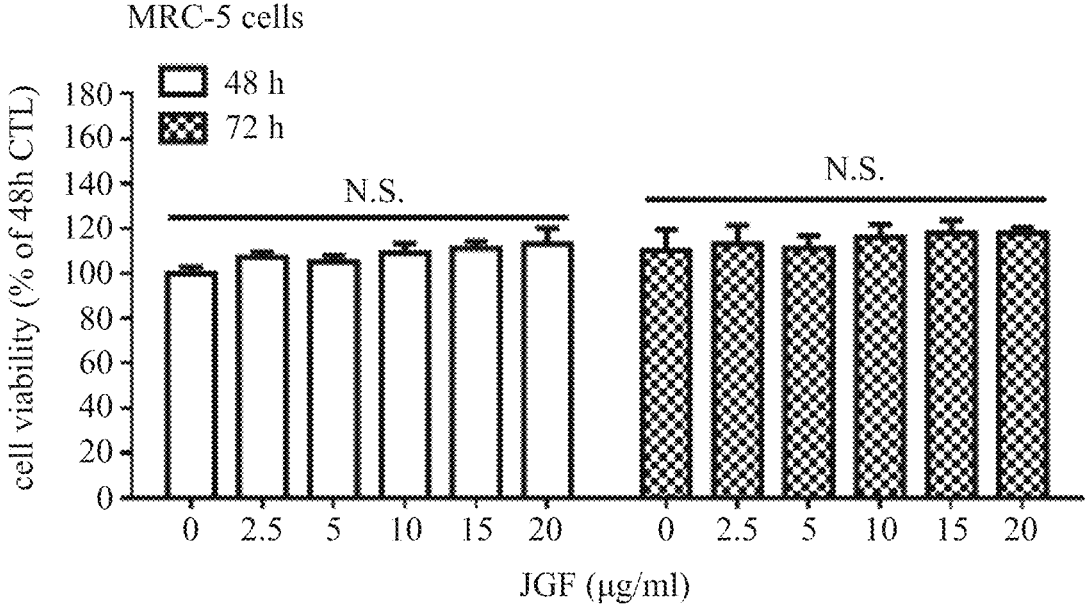

Pharmacological Example 4: JGF Shows No Cytotoxic Effect on Human Fibroblast WI-38 and MRC-5 Cells Two human lung cell lines, epithelial WI-38 and fibroblast MRC-5, were used to determine the cytotoxic effect of JGF. A crystal violet assay was used to determine the concentration at which JGF inhibits activity in human lung cells. As shown in FIGS. 2A and 2B, it was found that JGF did not exhibit the cytotoxicity to either WI-38 or MRC-5 cells, and therefore, JGF is safe and non-toxic to cells.

Pharmacological Example 5: JGF Induced Lysosome-Dependent Degradation of ACE2

A shown above in FIGS. 1A to 1D, it was found that JGF effectively interrupted the interaction between the spike protein and the ACE2 receptor and suppressed membrane fusion, which plays a role in viral infection. The mechanisms by which JGF inhibited infection of normal human lung cells with SARS-CoV-2 were further examined.

It has been shown that SARS-CoV-2 infection is prevented by targeting ACE2 in lung cells to block the SARS-CoV-2 spike receptor from binding with ACE2. Therefore, it is further investigated to show JGF's effect on the protein levels of ACE2 in WI-38 and MRC5 cells.

Figure 3A:
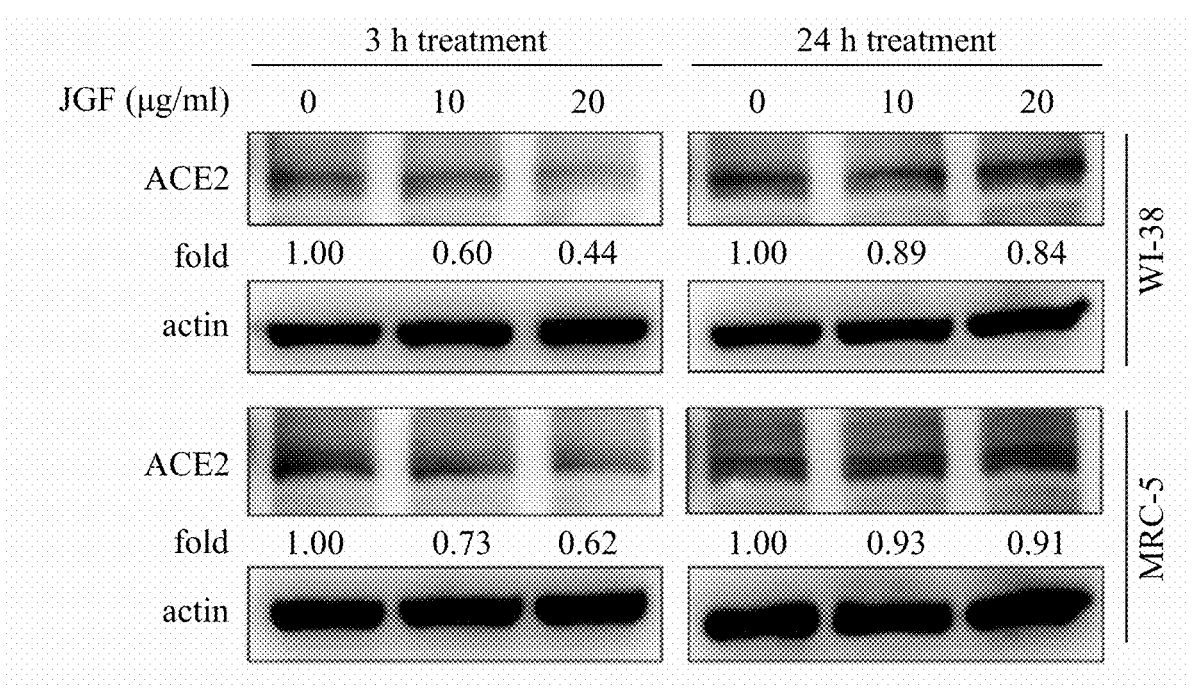
FIGS. 3A to 3E show that the herbal compositions of the JGF induce lysosome dependent degradation of ACE2.
Figure 3B:
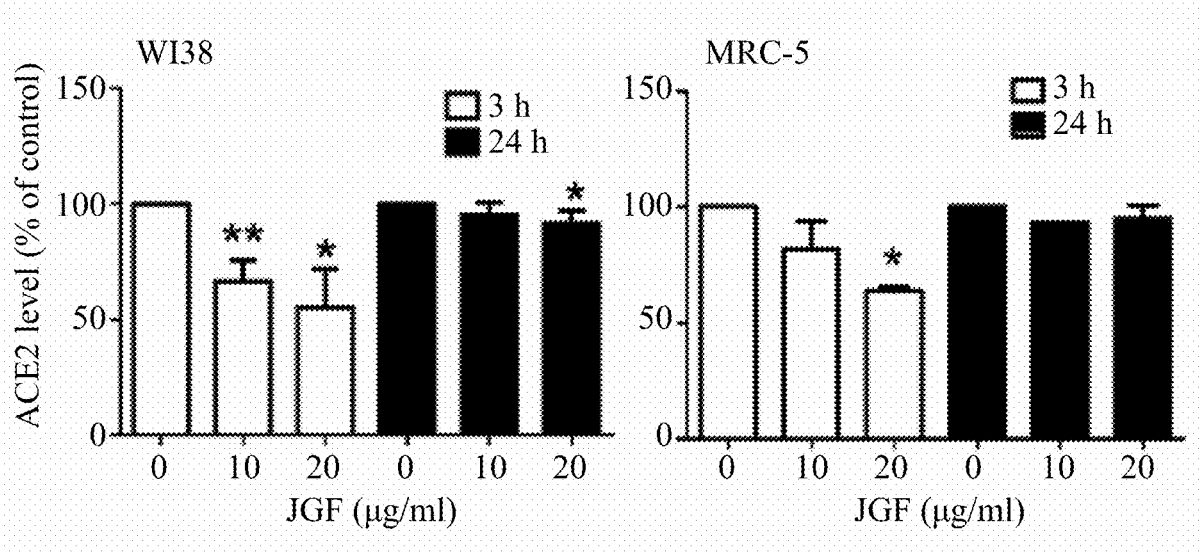

As shown in FIGS. 3A and 3B, it was found that brief treatment with JGF dramatically reduced the expressions of ACE2 by about 40 to 50% in a 3-hour treatment, but the ACE2 level increased when treated with JGF for a longer period (24 hours). These results suggest that JGF temporarily downregulates the ACE2 level to reduce infection with SARS-CoV-2.

Figure 3C:
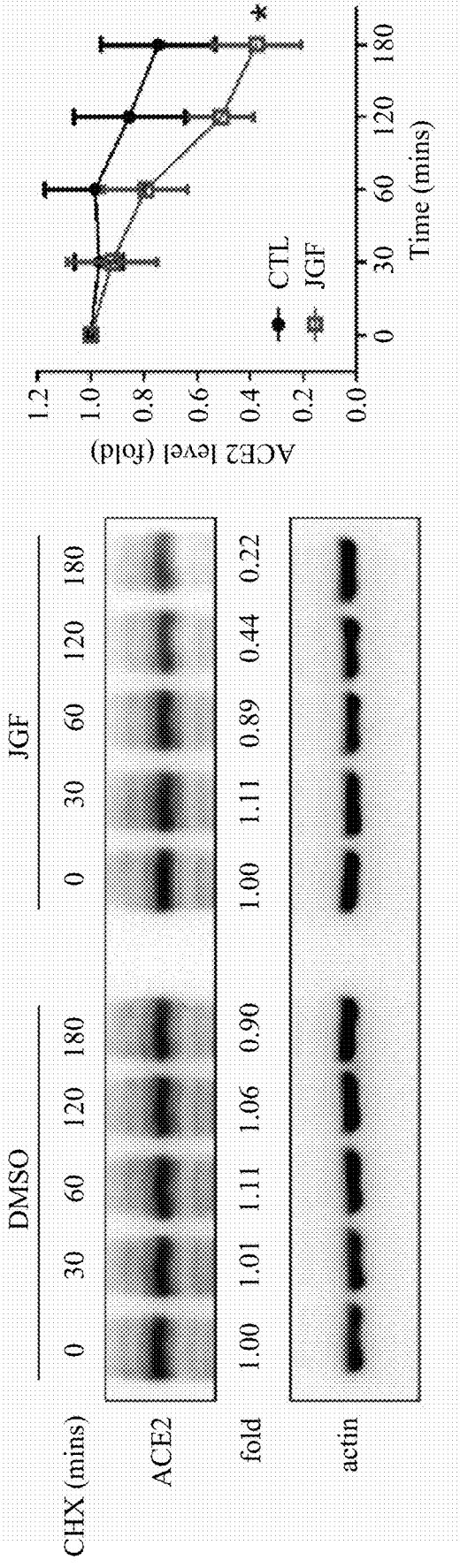
Figure 3D:
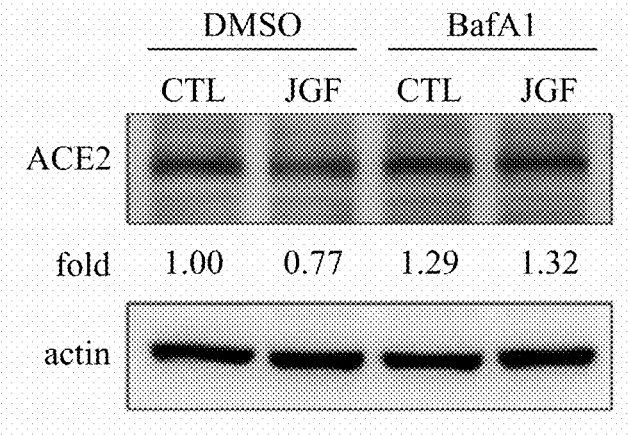
Figure 3E:
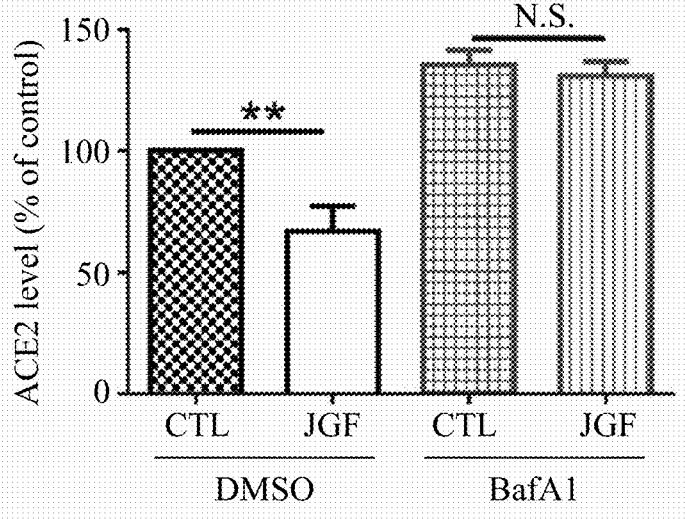

These results showed that JGF significantly suppressed the total protein levels of ACE2 within a short period of time. Therefore, the mechanism by which JGF downregulated ACE2 levels was further examined. For example, it was examined whether JGF-induced ACE2 degradation is dependent on proteasome or lysosomal systems. Initially, the half-life of ACE2 in WI-38 cells was analyzed following treatment with cycloheximide (CHX), which is a ribosome inhibitor that blocks protein synthesis. It was found that when WI-38 cells were co-treated with JGF and CHX, the level of ACE2 was dramatically downregulated in a time-dependent manner, as shown in FIG. 3C, suggesting that JGF could induce degradation of ACE2. Next, using the lysosome inhibitor, BafA1, we found that BafA1 recovered the ACE2 level in WI38 cells after JGF treatment, as shown in FIGS. 3D and 3E.

These results indicated that JGF can be used to prevent SARS-CoV-2 infection by inducing ACE2 degradation.

Pharmacological Example 6: JGF Downregulates TMPRSS2 Levels

Figure 4A:
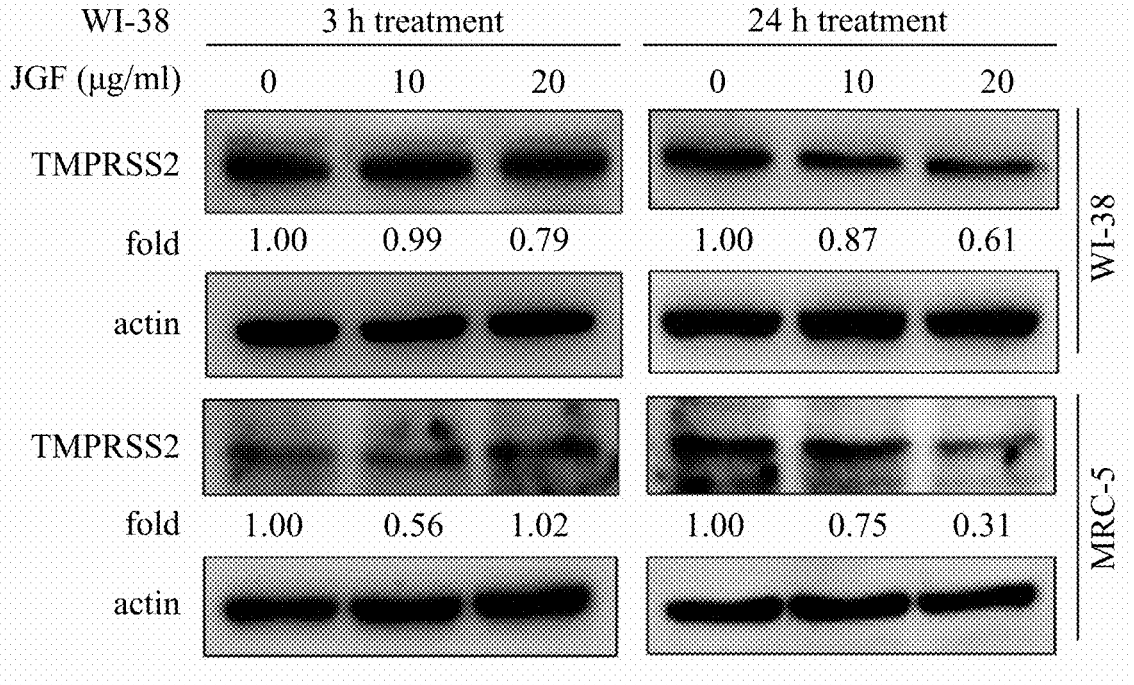
FIGS. 4A to 4C show that the herbal compositions of the JGF reduce TMPRSS2 levels in WI-38 and MRC-5 cells.
Figure 4B:
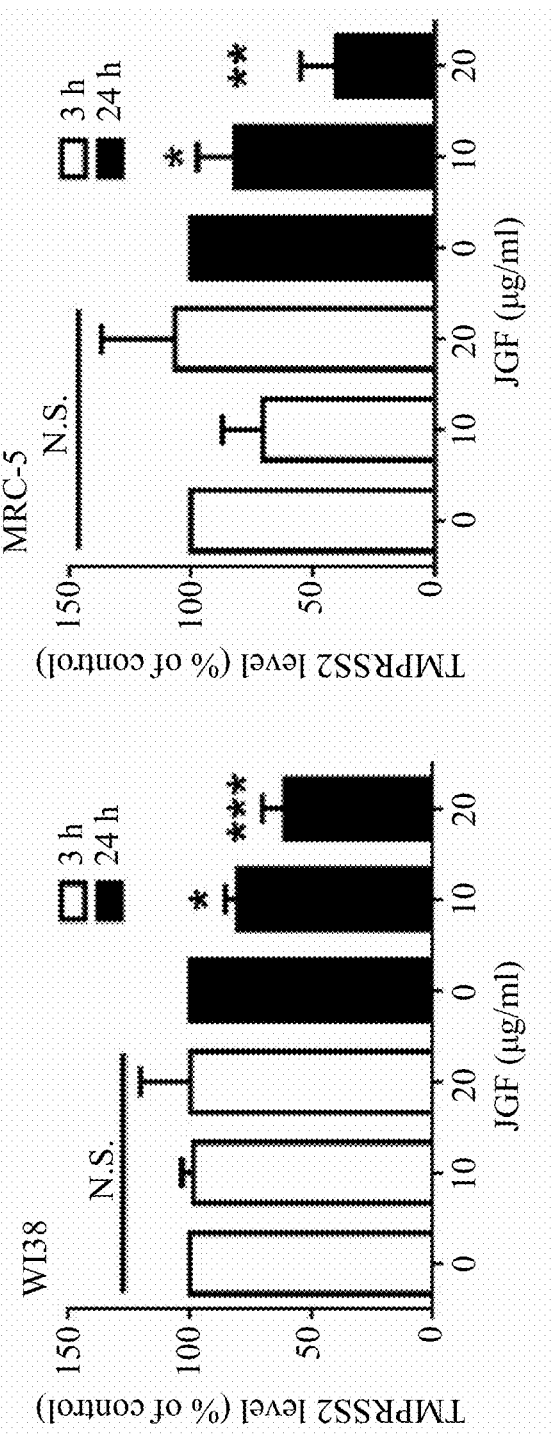
Figure 4C:
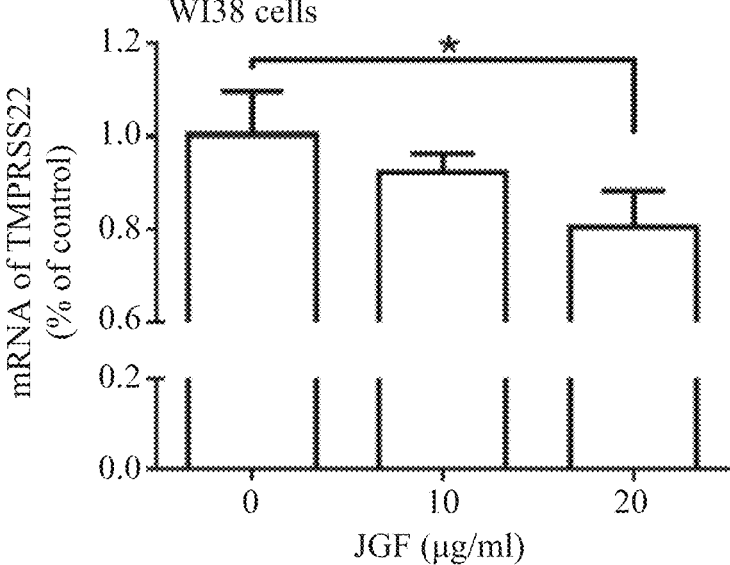
Figure 4C:
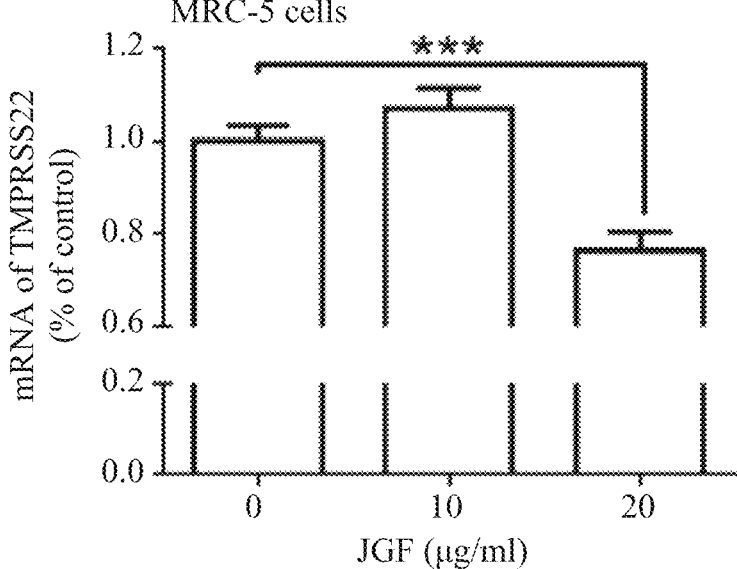

TMPRSS2 is another membrane protein playing a role for SARS-CoV-2 infection. Therefore, it was further examined whether JGF affected the expression of TMPRSS2 in WI38 and MRC-5 cells. As shown in FIGS. 4A and 4B, it was found that JGF did not affect the expression of TMPRSS2 within a short period of time. However, long-term treatment with JGF effectively downregulated the expression of TMPRSS2 by 40 to 70%. In parallel, JGF significantly reduced mRNA of TMPRSS2 for the 24 h treatment, as shown in FIG. 4C. These results suggested that JGF regulates the signaling transductions which control the synthesis of TMPRSS2.

Pharmacological Example 7: JGF Downregulates the Expressions of ACE2 and TMPRSS2 in Multiple Organs of Mice It is known that ACE2 and TMPRSS2 are expressed in several human organs. For example, ACE2 is abundantly present in the epithelia of the lung and small intestine. The mRNA expressions for both ACE2 and TMPRSS2 have been detected in the heart, digestive tract, kidney, and brain, as suggested by M. Dong, J. Zhang, X. Ma, J. Tan, L. Chen, S. Liu, Y Xin, and L. Zhuang, "ACE2, TMPRSS2 distribution and extrapulmonary organ injury in patients with COVID-19," Biomed. Pharmacother. 131 (2020) 110678.

Therefore, the levels of ACE2 and TMPRSS2 in lung, brain, colon, and kidney tissues of mice were examined.

Figure 5A:
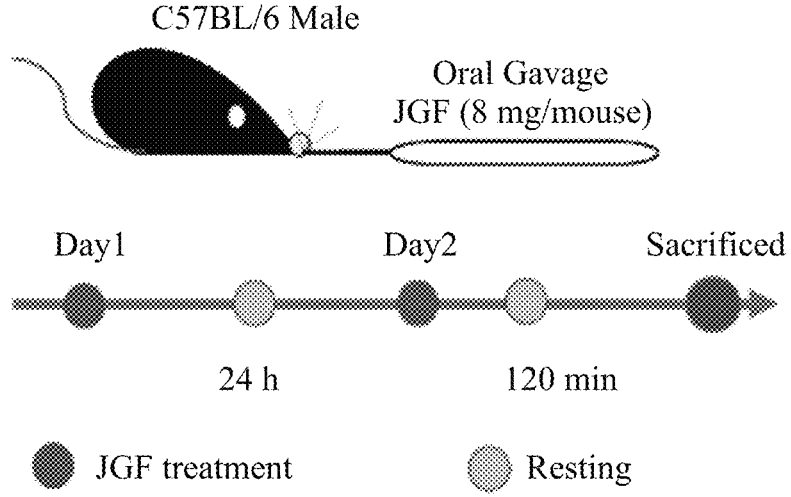
FIGS. 5A to 5I show the effect of herbal compositions of the JGF on ACE2 and TMPRSS2 levels in lung tissues of mouse model.
Figure 5B:
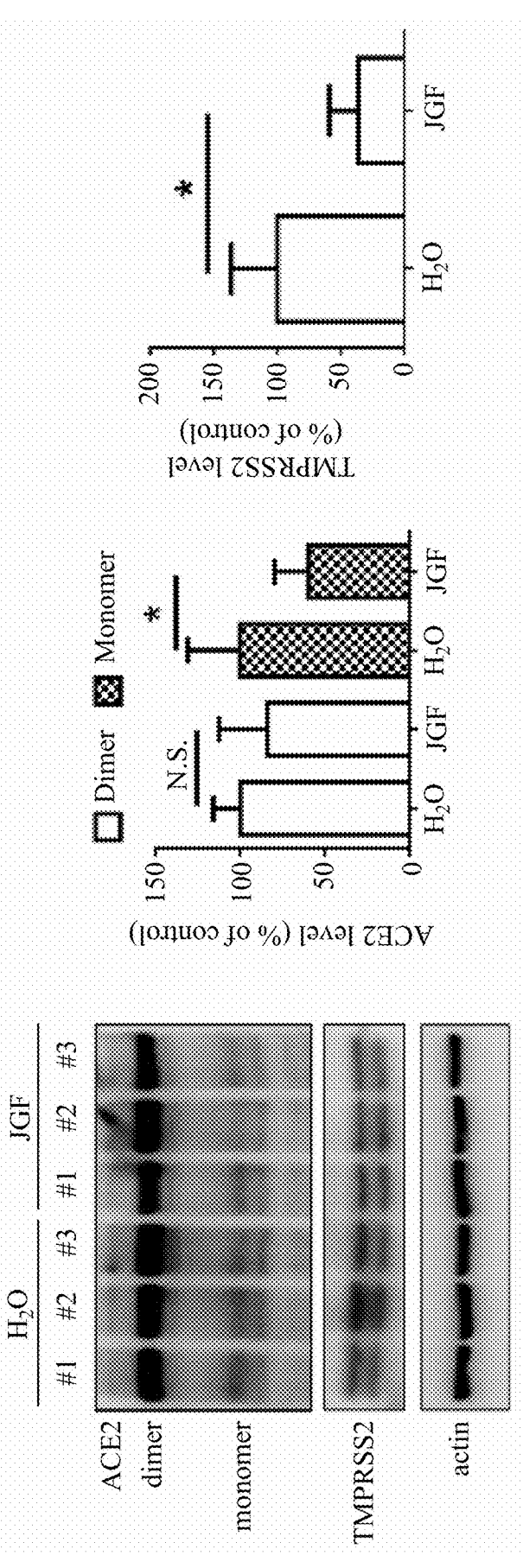

To determine whether JGF affected the levels of ACE2 and TMPRSS2 in those organs of mice, a series of in vivo experiments were carried out. Initially, the effect of orally ingested JGF on mice in vivo was investigated. Continuous feeding with JGF for 2 days effectively reduced protein levels of ACE2 and TMPRSS2 in the lungs of mice, as shown in FIGS. 5A and 5B. For example, it was found that in the mice receiving the administration of JGF, the monomer of ACE levels was significantly reduced by 45%; however, the dimer form of ACE2 was not reduced in lung tissues. On the other hand, JGF reduced protein levels of TMPRSS2 by 50%, also shown in FIG. 5B.

Figure 5C:
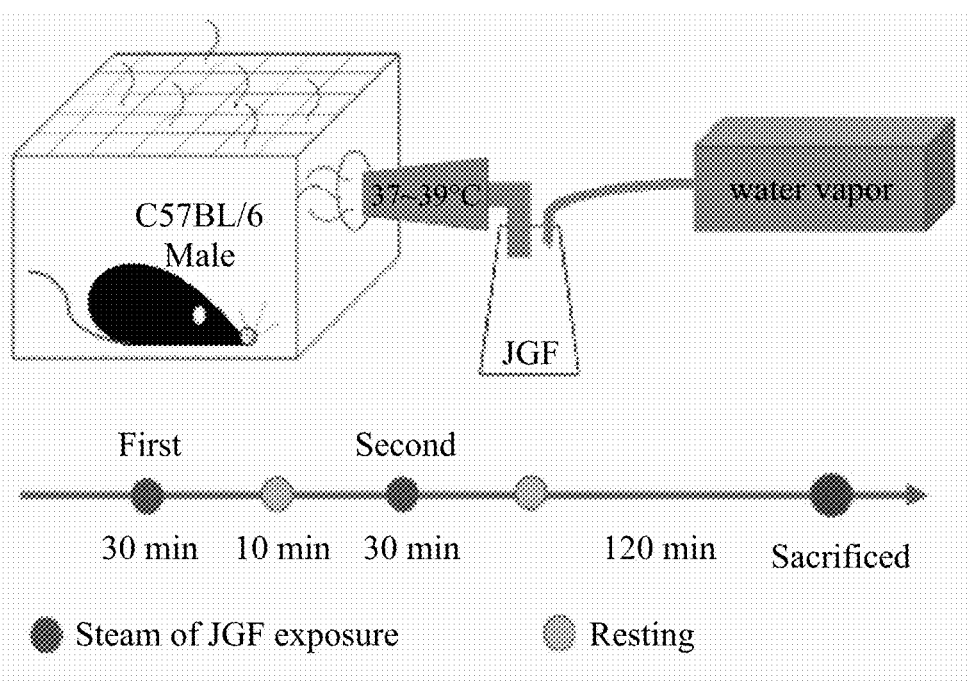
Figure 5D:
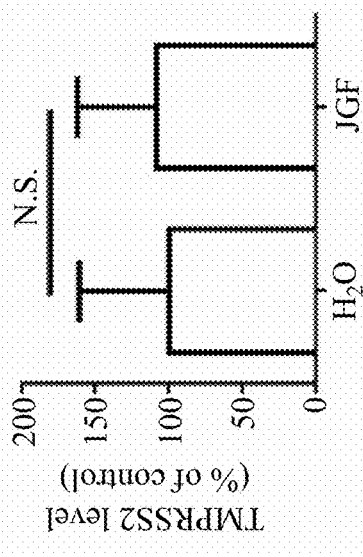
Figure 5D:
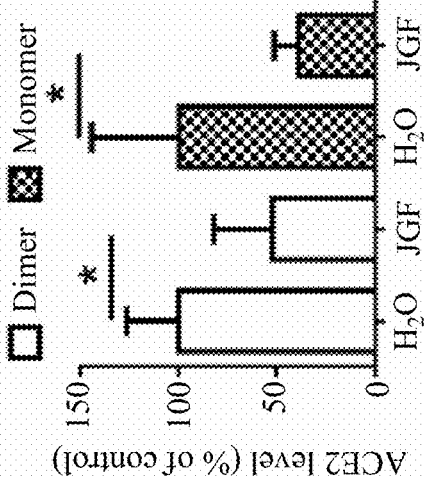
Figure 5D:
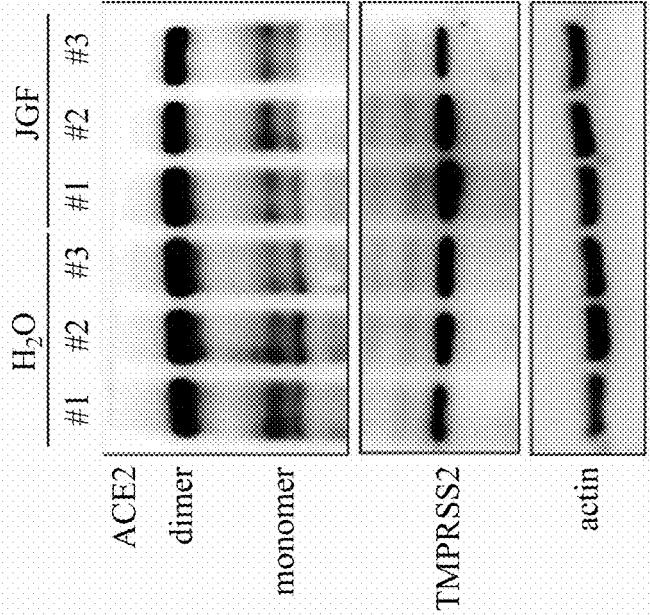

In addition, in the view of traditional *Chinese* medicine, drugs could be absorbed through the nasal cavity by a steam method, which can make the herbal medicine quickly enter the nasal cavity and lungs to address cold symptoms. The steam method was also adopted and used with the mice to inhale JGF, as shown in FIG. 5C. As shown in FIG. 5D, it was found that ACE2 (both monomer and dimer) was reduced by more than 50% after the mice inhale JGF; however, TMPRSS2 levels were unchanged after the short-term exposure to JGF.

Figure 5E:
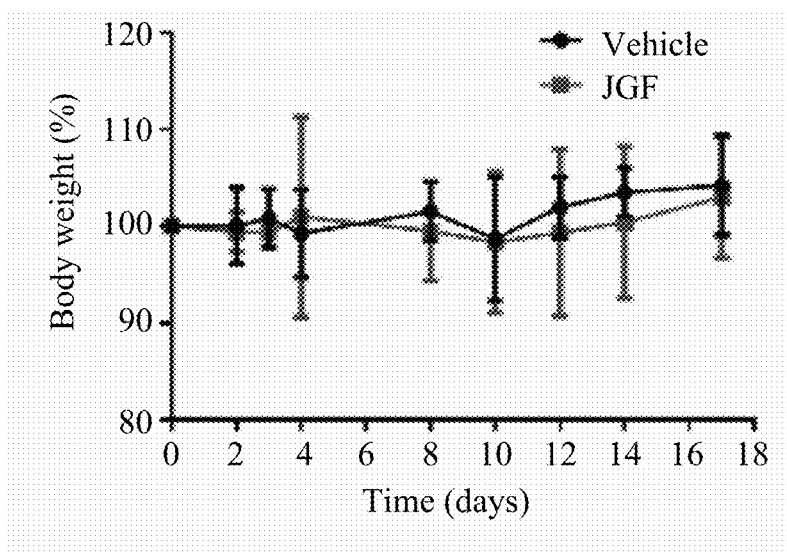
Figure 5F:
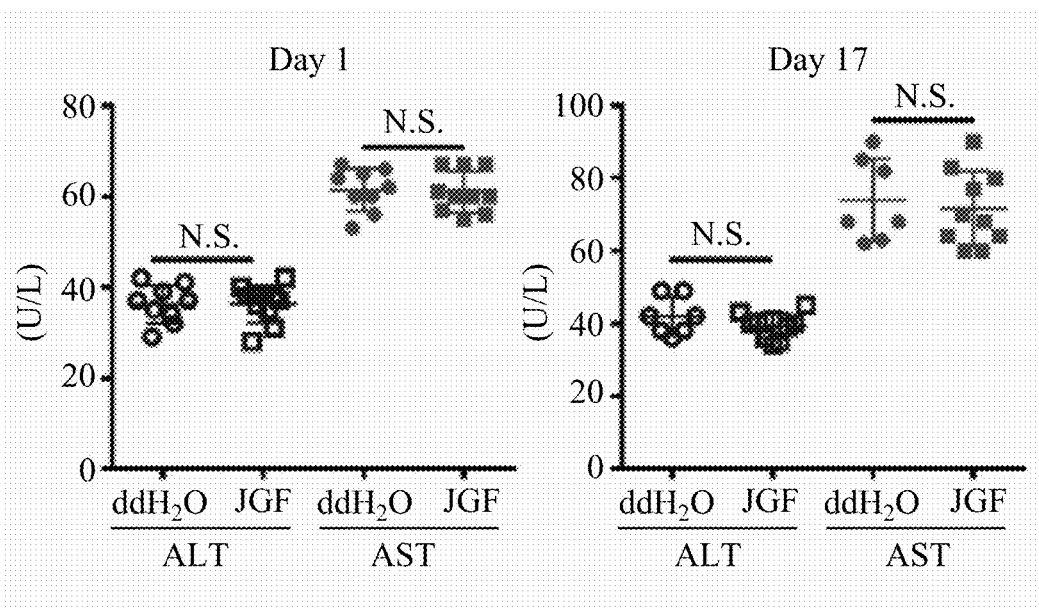
Figure 5G:
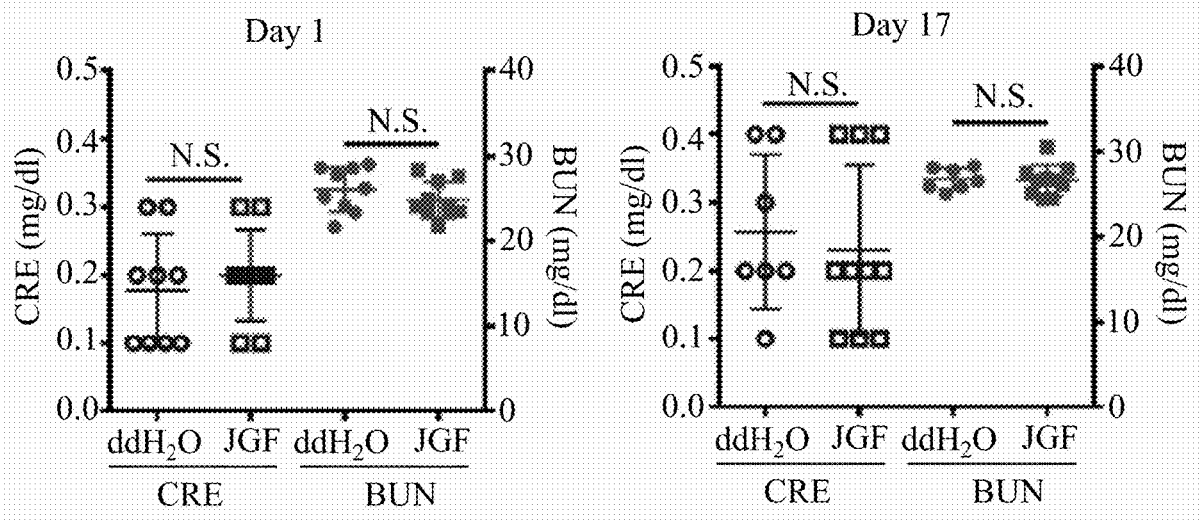
Figure 5H:
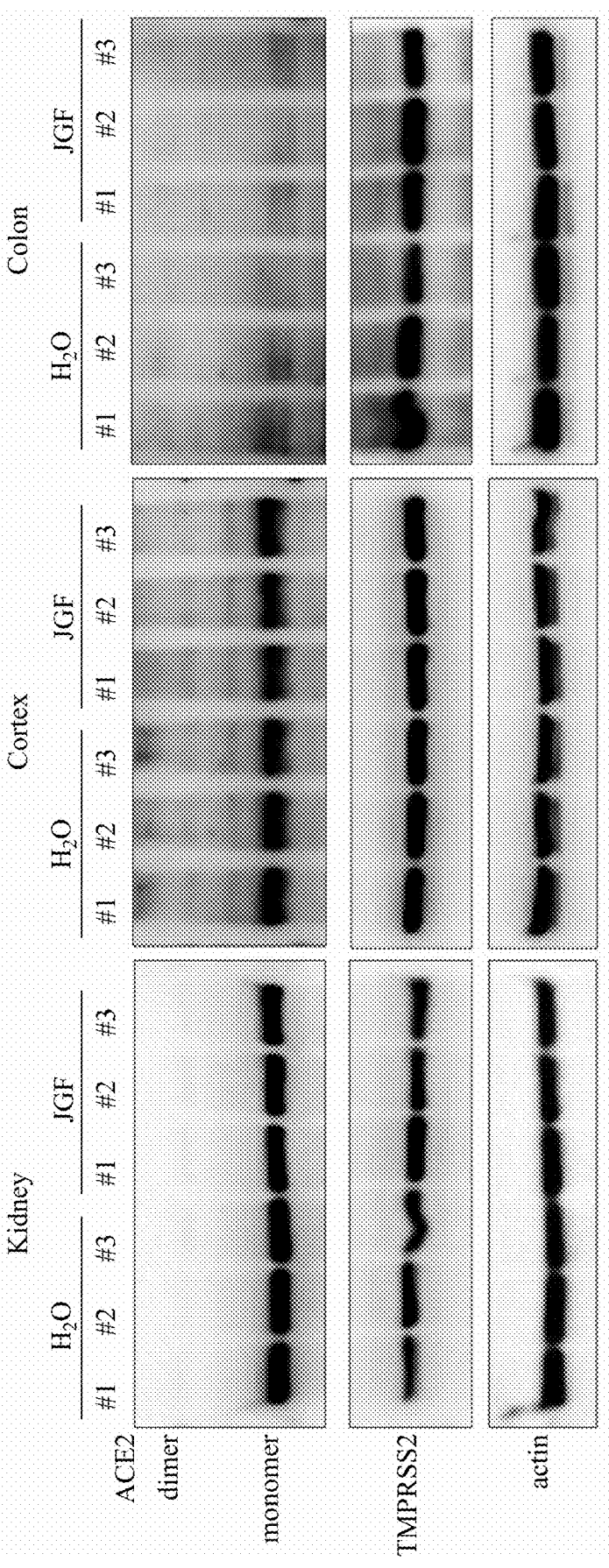
Figure 5I:
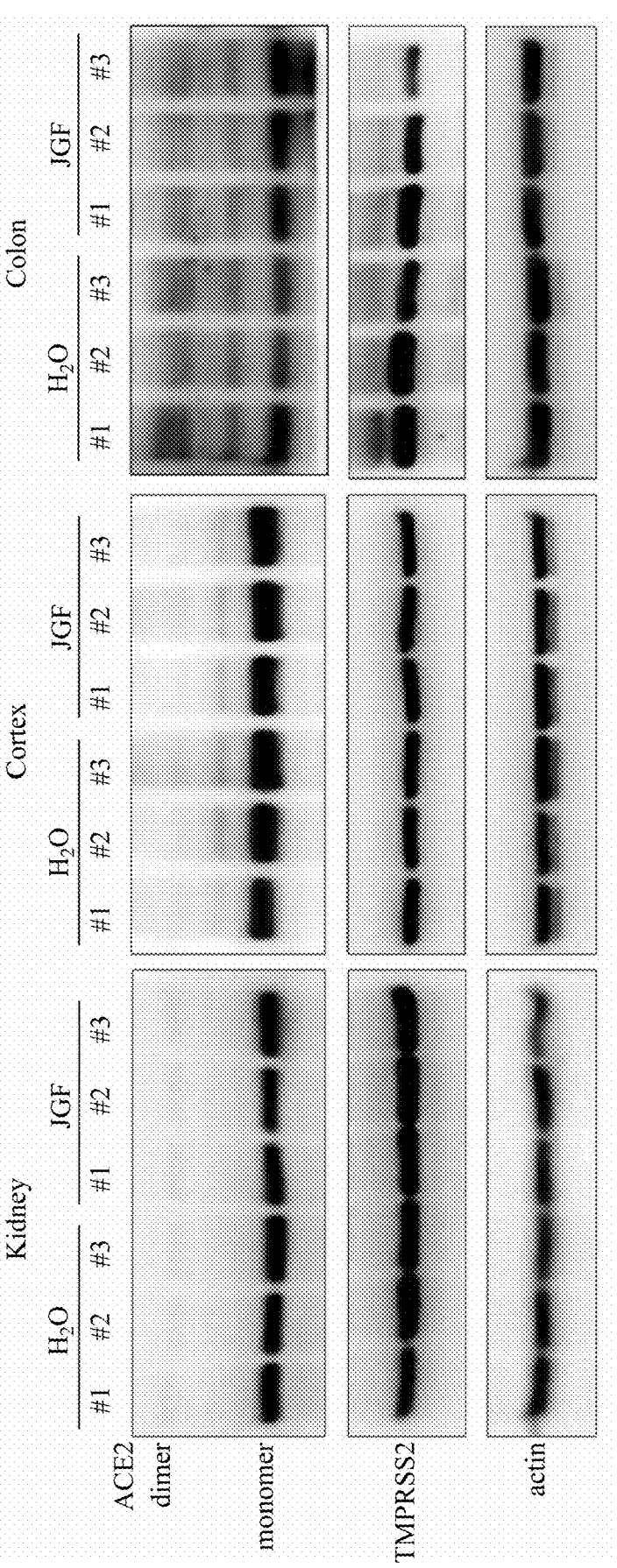

Also, it was found that JGF did not affect body weight of mice as shown in FIG. 5E. Furthermore, to examine the degree of liver and kidney injury in mice that were fed with JGF, the aspartate aminotransferase (AST)/alanine amino-transferase (ALT) and blood urea nitrogen (BUN)/creatinine (CRE) levels were analyzed in blood samples at the end of JGF treatment. The results shown in FIGS. 5F and 5G indicated that JGF neither affects liver functions nor causes kidney toxicity in the mouse model. These results suggest that JGF may reduce infection with SARS-CoV-2 without side effects. Also, FIGS. 5H and 5I show that JGF treatment did not alter expression levels of ACE2 and TMPRSS2 in other tissues including kidney, cortex and colon.

Pharmacological Example 8: JGF Inhibits the Formation of Plaque Formation for SARS-CoV-2 on Vero E6 Cells The above showed that JGF prevents viruses from infecting cells by reducing ACE2 and TMPRSS2. Therefore, it was further investigated whether JGF could inhibit the infection and proliferation of SARS-CoV-2.

The Vero E6 cells were chosen for investigating the SARS-CoV-2 infection. Initially, the effects of JGF on cell viability of Vero E6 cells were examined. As shown in FIG. 6A, it was found that JGF did not exhibit a cytotoxic effect on Vero E6 cells even at a high concentration of JGF. A cytotoxic concentration of 50 ($CC_{50}$) was higher than 800 μg/mL.

Next, virus plaque formation assay was conducted to examine the efficacy of JGF in preventing SARS-CoV-2 infection. Vero E6 cells were pretreated with JGF before SARS-CoV-2 infection, as shown in FIG. 6B. It was found that JGF dramatically inhibited plaque formation in a concentration-dependent manner, compared to the anti-viral drug used for COVID-19, remdesivir (REM) at 2 μM, as shown in FIG. 6C. For example, JGF at 200 μg/mL reduced plaque formation of SARA-CoV-2 by 70%. Taken together, these results suggest that JGF reduces SARS-CoV-2 infection and proliferation.

Pharmacological Example 9: JGLF Downregulates the Expressions of ACE2 and TMPRSS2, and Shows the Anti-Inflammation Effects As shown in FIGS. 9A and 9B, JGLF dose-dependently inhibited the protein expression of ACE2 in the short-term treatment (3 h) in WI38 cells; however, TMPRSS2 levels were unchanged after the short-term exposure to JGF. On the other hand, JGLF reduced the protein expression of TMPRSS2 by 60% for the long-term treatment (24 h) at highest concentration without affecting ACE2 levels. The above data showed that JGLF prevents viruses from infecting cells by reducing ACE2 and TMPRSS2. Therefore, it was further investigated whether JGLF could inhibit the inflammation.

It was found that JGLF doesn't affect the viability of macrophages, nor does it induce the production of inflammatory factor NO, and therefore, JGLF is as safe as JGF and non-toxic to cells compared to LPS as shown in FIGS. 9C and 9D. Moreover, in the presence of LPS (shown in FIGS. 9E and 9F), JGLF did not affect the viability of macrophage cells stimulated by LPS but inhibited NO production. That said, after stimulating inflammation in macrophages by LPS, JGLF did not affect cell survival but inhibits LPS-induced NO production.

Lastly, in macrophages treated with or without LPS, JGLF alone slightly induced the inflammatory factor of interleukin-6 (shown in FIG. 9G), but significantly inhibited LPS-induced interleukin-6 production (shown in FIG. 9H).

Pharmacological Example 10: JGEF Downregulates the Expressions of TMPRSS2, and Shows the Anti-Inflammation Effects As shown in FIGS. 10A and 10B, JGEF affected protein expression of ACE2 in the short-term treatment and the expression of TMPRSS2 for the long-term treatment in WI38 cells. Next, the effect of JGEF on inflammation in RAW26.7 cells was further investigated. Similar to JGLF, JGEF alone did not affect the viability of macrophages (shown in FIG. 10C), nor did it induce the production of inflammatory factor NO (shown in FIG. 10D). In the presence of LPS, as shown in FIGS. 10E and 10F, viability of macrophage was not affected by JGEF, but NO production of LPS-stimulated macrophages was inhibited.

Furthermore, in macrophages, JGEF alone versus LPS did not affect the inflammatory factor interleukin-6 (shown in FIG. 10G), but inhibited LPS-induced interleukin-6 production (shown in FIG. 10H).

Figure 11C:
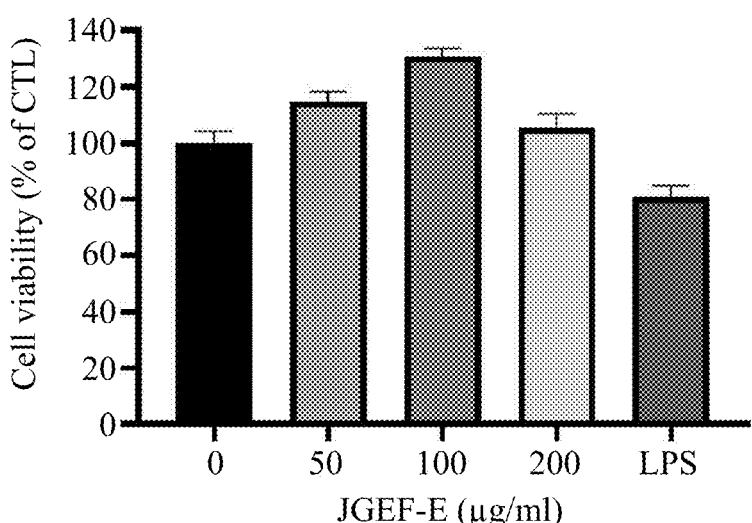
Figure 11D:
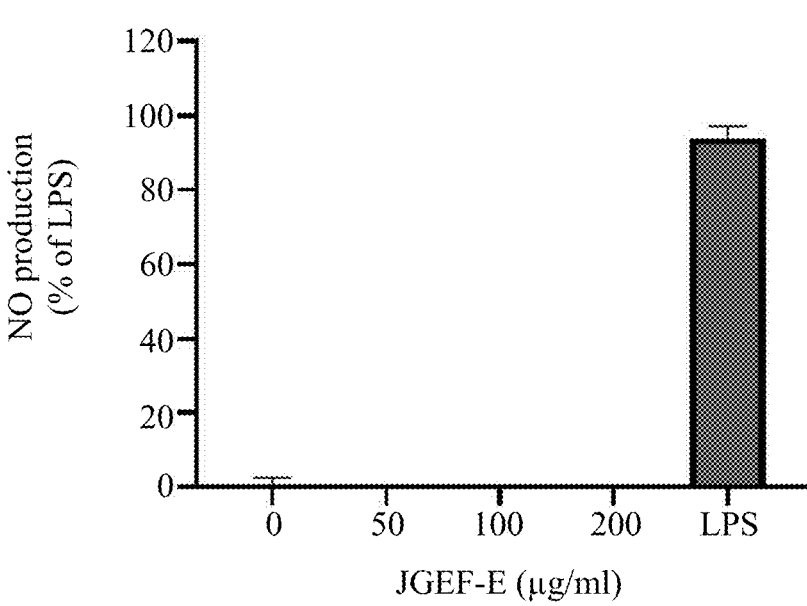
Figure 11E:
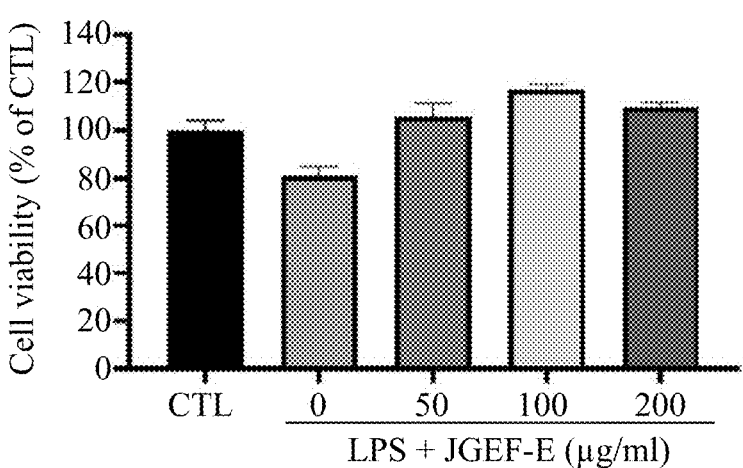
Figure 11F:
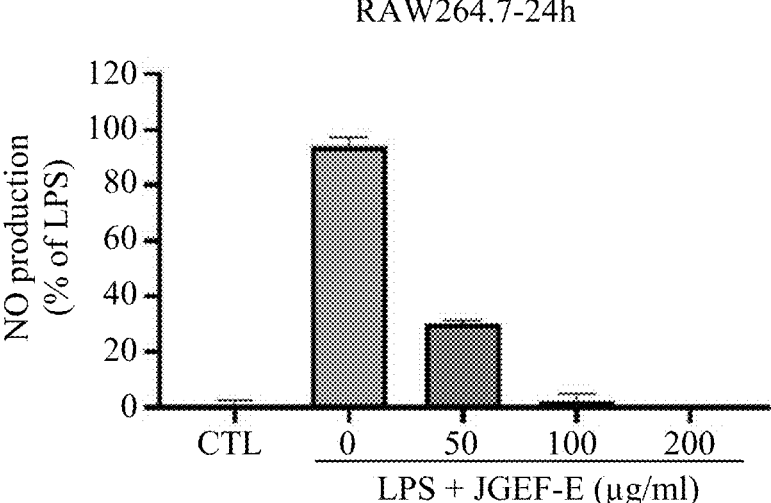

Pharmacological Example 11: JGEF-E Downregulates the Expressions of TMPRSS2, and Shows the Anti-Inflammation Effects Firstly, JGEF-E inhibited the protein expression of TMPRSS2 but doesn't affect the protein expression of ACE2 as shown in FIGS. 11A and 11B. Secondly, JGEF-E did not affect the activity of macrophages, nor did it induce the production of the inflammation-factor NO versus LPS, as shown in FIGS. 11C and 11D. Lastly, JGEF-E did not affect the viability of macrophage cells stimulated by LPS, but inhibited NO production of LPS-stimulated macrophages as shown in FIGS. 11E and 11F.

While some of the embodiments of the present disclosure have been described in detail above, it is, however, possible for those of ordinary skill in the art to make various modifications and changes to the embodiments shown without substantially departing from the teaching and advantages of the present disclosure. Such modifications and changes are thus encompassed in the scope of the present disclosure as set forth in the appended claims.

---

---

What is claimed is:

1. A herbal composition for treating a viral infection, comprising a decoction of a combination of herbs and a pharmaceutically acceptable carrier thereof, wherein the viral infection is caused by a coronavirus, and wherein the combination of herbs comprises *Forsythia suspensa, Scutellaria baicalensis, Bupleurum chinense*, and *Agastache rugosa*; and at least one selected from the group consisting of *Magnolia officinalis, Astragalus membranaceus, Atractylodes macrocephala*, and seeds of *Ligustrum lucidum*, and wherein the decoction comprises a water extract or an ethanol extract, and wherein the combination of herbs comprises, based on a total weight thereof, 25% to 35% by weight of Forsythia suspensa, 18% to 26% by weight of *Scutellaria baicalensis,* 15% to 25% by weight of *Bupleurum chinense*, and 7% to 15% by weight of *Agastache rugosa*; and at least one selected from the group consisting of 15% to 25% by weight of *Magnolia officinalis,* 25% to 35% by weight of *Astragalus membranaceus,* 7% to 15% by weight of seeds of *Ligustrum lucidum*, and 7% to 15% by weight of *Atractylodes macrocephala.*

2. A method for preparing the herbal composition of claim 1, comprising: extracting the combination of herbs with an extracting solution including at least one of water and ethanol by boiling; and removing solids from the extract to obtain the decoction.

3. The method of claim 2, wherein the extracting comprises boiling the combination of herbs in the extracting solution for at least an hour.

4. The method of claim 3, wherein the extracting comprises boiling the combination of herbs in the extracting solution for 2 to 4 hours.

5. The method of claim 2, wherein the extracting comprises boiling the combination of herbs in the extracting solution at a temperature of at least 70° C.

6. The method of claim 5, wherein the extracting comprises boiling the combination of herbs in the extracting solution at a temperature of 100° C. to 120° C.

7. The method of claim 2, wherein the extracting comprises boiling the combination of herbs in the extracting solution at an atmospheric pressure of at least 1 atm.

8. The method of claim 7, wherein the extracting comprises boiling the combination of herbs in the extracting solution at an atmospheric pressure of 1.1 atm to 1.3 atm.

9. The method of claim 2, wherein a weight ratio of the combination of herbs to the extracting solution is from 0.5:1 to 5:1.

10. A method for treating a viral infection in a subject in need thereof, comprising administering to the subject a therapeutically effective amount of the herbal composition of claim 1, wherein the viral infection is caused by a coronavirus.

11. The method of claim 10, wherein the coronavirus is severe acute respiratory syndrome coronavirus (SARS-CoV), Middle East respiratory syndrome coronavirus (MERS-CoV), SARS-CoV-2, mouse hepatitis virus (MHV), or porcine epidemic diarrhea virus (PEDV).

12. The method of claim 10, wherein the coronavirus is a variant of SARS-CoV-2.

* * * * *

SEQUENCE LISTING

```
Sequence total quantity: 4
SEQ ID NO: 1              moltype = DNA  length = 22
FEATURE                   Location/Qualifiers
source                    1..22
                          mol_type = other DNA
                          organism = Homo sapiens
SEQUENCE: 1
cctctaactg gtgtgatggc gt                                             22

SEQ ID NO: 2              moltype = DNA  length = 22
FEATURE                   Location/Qualifiers
source                    1..22
                          mol_type = other DNA
                          organism = Homo sapiens
SEQUENCE: 2
tgccaggact tcctctgaga tg                                             22

SEQ ID NO: 3              moltype = DNA  length = 20
FEATURE                   Location/Qualifiers
source                    1..20
                          mol_type = other DNA
                          organism = Homo sapiens
SEQUENCE: 3
tggtatcgtg gaaggactca                                                20

SEQ ID NO: 4              moltype = DNA  length = 20
FEATURE                   Location/Qualifiers
source                    1..20
                          mol_type = other DNA
                          organism = Homo sapiens
SEQUENCE: 4
agtgggtgtc gctgttgaag                                                20
```